United States Patent
Pottorf et al.

(10) Patent No.: US 9,612,231 B2
(45) Date of Patent: Apr. 4, 2017

(54) EXPLORATION METHOD AND SYSTEM FOR DETECTION OF HYDROCARBONS

(71) Applicants: Robert J. Pottorf, Houston, TX (US); Leonard J. Srnka, Bellaire, TX (US); William Bond, Sugar Land, TX (US); Sebastien L. Dreyfus, Houston, TX (US); Michael Lawson, Houston, TX (US); William P. Meurer, Pearland, TX (US); Daniel P. Cherney, Hampton, NJ (US); Steven R. May, Missouri City, TX (US); William G. Powell, Houston, TX (US); Christoper J. Vandewater, Houston, TX (US); Mehmet D. Ertas, Bethlehem, PA (US); Sumathy Raman, Annandale, NJ (US); Aaron B. Regberg, Houston, TX (US); A. Lucie N'Guessan, Houston, TX (US); Amelia C. Robinson, Houston, TX (US); Kurt W. Rudolph, Houston, TX (US)

(72) Inventors: Robert J. Pottorf, Houston, TX (US); Leonard J. Srnka, Bellaire, TX (US); William Bond, Sugar Land, TX (US); Sebastien L. Dreyfus, Houston, TX (US); Michael Lawson, Houston, TX (US); William P. Meurer, Pearland, TX (US); Daniel P. Cherney, Hampton, NJ (US); Steven R. May, Missouri City, TX (US); William G. Powell, Houston, TX (US); Christoper J. Vandewater, Houston, TX (US); Mehmet D. Ertas, Bethlehem, PA (US); Sumathy Raman, Annandale, NJ (US); Aaron B. Regberg, Houston, TX (US); A. Lucie N'Guessan, Houston, TX (US); Amelia C. Robinson, Houston, TX (US); Kurt W. Rudolph, Houston, TX (US)

(73) Assignee: ExxonMobil Upstream Research Company, Spring, TX (US)

( * ) Notice: Subject to any disclaimer, the term of this patent is extended or adjusted under 35 U.S.C. 154(b) by 85 days.

(21) Appl. No.: 14/350,773

(22) PCT Filed: Nov. 9, 2012

(86) PCT No.: PCT/US2012/064548
§ 371 (c)(1),
(2) Date: Apr. 9, 2014

(87) PCT Pub. No.: WO2013/071185
PCT Pub. Date: May 16, 2013

(65) Prior Publication Data
US 2014/0256055 A1 Sep. 11, 2014

Related U.S. Application Data

(63) Continuation-in-part of application No. PCT/US2012/052542, filed on Aug. 27, 2012.
(Continued)

(51) Int. Cl.
*G01N 31/16* (2006.01)
*G01N 33/24* (2006.01)
(Continued)

(52) U.S. Cl.
CPC ............ *G01N 33/241* (2013.01); *G01N 1/00* (2013.01); *G01N 29/14* (2013.01); *G01V 1/38* (2013.01);
(Continued)

(58) Field of Classification Search
None
See application file for complete search history.

(56) References Cited

U.S. PATENT DOCUMENTS 3,835,710 A   9/1974   Pogorski
3,862,576 A   1/1975   Pogorski
(Continued)

FOREIGN PATENT DOCUMENTS

| | | |
|---|---|---|
| EP | 2113796 | 11/2009 |
| GB | 2478511 | 9/2011 |

(Continued)

OTHER PUBLICATIONS

Aeschbach-Hertig, W., et al., (2000), "Palaeotemperature reconstruction from noble gases in ground water taking into account equilibrium with entrapped air", *Nature*, 405, pp. 1040-1044.

(Continued)

*Primary Examiner* — Robert Xu
(74) *Attorney, Agent, or Firm* — ExxonMobil Upstream Research Company—Law Department

(57) ABSTRACT

A method for detecting hydrocarbons is described. The method includes performing a remote sensing survey of a survey location to identify a target location. Then, an underwater vehicle (UV) is deployed into a body of water and directed to the target location. The UV collects measurement data within the body of water at the target location, which is then analyzed to determine whether hydrocarbons are present at the target location.

12 Claims, 5 Drawing Sheets

Related U.S. Application Data

(60) Provisional application No. 61/558,822, filed on Nov. 11, 2011, provisional application No. 61/595,394, filed on Feb. 6, 2012, provisional application No. 61/616,813, filed on Mar. 28, 2012.

(51) Int. Cl.

| | |
|---|---|
| *G01V 9/00* | (2006.01) |
| *G01N 1/00* | (2006.01) |
| *G01N 29/14* | (2006.01) |
| *G01V 1/38* | (2006.01) |
| *G01V 3/08* | (2006.01) |
| *G01V 8/02* | (2006.01) |
| *G01V 5/00* | (2006.01) |
| *B63G 8/00* | (2006.01) |
| *G01V 8/00* | (2006.01) |
| *G06F 19/00* | (2011.01) |
| *G01V 11/00* | (2006.01) |

(52) U.S. Cl.
CPC .............. *G01V 3/08* (2013.01); *G01V 3/081* (2013.01); *G01V 9/005* (2013.01); *G01V 9/007* (2013.01); *B63G 8/001* (2013.01); *G01V 5/00* (2013.01); *G01V 8/00* (2013.01); *G01V 8/02* (2013.01); *G01V 11/00* (2013.01); *G06F 19/00* (2013.01)

(56) References Cited

U.S. PATENT DOCUMENTS

| | | |
|---|---|---|
| 3,961,187 A | 6/1976 | Barringer |
| 4,001,764 A | 1/1977 | Holland et al. |
| 4,378,055 A | 3/1983 | Bartz |
| 4,434,364 A | 2/1984 | Correa et al. |
| 4,560,664 A | 12/1985 | Demaison et al. |
| 4,833,915 A | 5/1989 | Radd et al. |
| 5,439,800 A | 8/1995 | Thompson |
| 5,798,982 A | 8/1998 | He et al. |
| 6,246,963 B1 | 6/2001 | Cross et al. |
| 6,509,566 B1 | 1/2003 | Wamsley et al. |
| 6,514,915 B1 | 2/2003 | Beyer et al. |
| 6,578,405 B2 | 6/2003 | Kleinberg et al. |
| 6,613,520 B2 | 9/2003 | Ashby |
| 6,645,769 B2 | 11/2003 | Tayebi et al. |
| 6,754,588 B2 | 6/2004 | Cross et al. |
| 6,810,332 B2 | 10/2004 | Harrison |
| 6,826,483 B1 | 11/2004 | Anderson et al. |
| 6,873,570 B2 | 3/2005 | Zhu et al. |
| 6,888,127 B2 | 5/2005 | Jones et al. |
| 6,985,841 B2 | 1/2006 | Barroux |
| 7,011,154 B2 | 3/2006 | Maher et al. |
| 7,124,030 B2 | 10/2006 | Ellis |
| 7,174,254 B2 | 2/2007 | Ellis |
| 7,210,342 B1 | 5/2007 | Sterner et |
| 7,249,009 B2 | 7/2007 | Ferworn et al. |
| 7,297,661 B2 | 11/2007 | Beyer et al. |
| 7,328,107 B2 | 2/2008 | Strack et al. |
| 7,337,660 B2 | 3/2008 | Ibrahim et al. |
| 7,387,021 B2 | 6/2008 | DiFoggio |
| 7,395,691 B2 | 7/2008 | Sterner et al. |
| 7,520,158 B2 | 4/2009 | DiFoggio |
| 7,526,418 B2 | 4/2009 | Pita et al. |
| 7,529,626 B1 | 5/2009 | Ellis |
| 7,596,480 B2 | 9/2009 | Fung et al. |
| 7,617,082 B2 | 11/2009 | Childs et al. |
| 7,687,769 B2 | 3/2010 | Indo et al. |
| 7,692,429 B2 | 4/2010 | MacGregor et al. |
| 7,704,746 B1 | 4/2010 | White et al. |
| 7,728,291 B2 | 6/2010 | Bello |
| 7,809,538 B2 | 10/2010 | Thomas |
| 7,969,152 B2 | 6/2011 | Velikhov et al. |
| 8,033,756 B2 | 10/2011 | Adamson |
| 8,071,295 B2 | 12/2011 | Ashby |
| 8,120,362 B2 | 2/2012 | Combee |
| 8,299,424 B2 | 10/2012 | Camilli |
| 8,316,934 B2 | 11/2012 | Pietrobon |
| 8,502,974 B2 | 8/2013 | Johnsen |
| 8,505,375 B2 | 8/2013 | Smalley |
| 8,577,613 B2 | 11/2013 | Bryant et al. |
| 8,695,703 B2 | 4/2014 | Dinariev et al. |
| 8,714,246 B2 | 5/2014 | Pop et al. |
| 8,908,476 B2 | 12/2014 | Chun et al. |
| 2002/0120429 A1 | 8/2002 | Ortoleva |
| 2005/0036404 A1* | 2/2005 | Zhu ............... G01S 15/8904 367/88 |
| 2006/0154306 A1 | 7/2006 | Kotlar et al. |
| 2008/0040086 A1 | 2/2008 | Betancourt et al. |
| 2008/0059140 A1 | 3/2008 | Salmon et al. |
| 2008/0097735 A1 | 4/2008 | Ibrahim et al. |
| 2008/0099241 A1 | 5/2008 | Ibrahim et al. |
| 2008/0147326 A1 | 6/2008 | Ellis |
| 2009/0071239 A1 | 3/2009 | Rojas et al. |
| 2009/0150124 A1 | 6/2009 | Wilt et al. |
| 2010/0012336 A1* | 1/2010 | Adamson ............ E02D 7/02 173/1 |
| 2010/0015612 A1 | 1/2010 | Pelham et al. |
| 2010/0086180 A1 | 4/2010 | Wallace |
| 2010/0153050 A1 | 6/2010 | Zumberge et al. |
| 2010/0155078 A1 | 6/2010 | Walters et al. |
| 2010/0257004 A1 | 10/2010 | Perlmutter et al. |
| 2010/0279290 A1 | 11/2010 | Sleat et al. |
| 2011/0004367 A1 | 1/2011 | Saunders et al. |
| 2011/0205536 A1* | 8/2011 | Johnsen ............... G01J 3/06 356/326 |
| 2011/0250582 A1 | 10/2011 | Gates et al. |
| 2011/0264430 A1 | 10/2011 | Tapscott et al. |
| 2011/0308790 A1 | 12/2011 | Strapoc et al. |
| 2012/0052564 A1 | 3/2012 | Shigeura et al. |
| 2012/0134749 A1* | 5/2012 | Darrah ............. E21B 47/1015 405/80 |
| 2014/0116318 A1 | 5/2014 | Brandt et al. |

(56) References Cited

U.S. PATENT DOCUMENTS

FOREIGN PATENT DOCUMENTS

| WO | 03/012390 | 2/2003 |
|---|---|---|
| WO | 2004/025261 | 3/2004 |
| WO | 2007/008932 | 1/2007 |
| WO | 2008/100614 | 8/2008 |
| WO | 2010/151842 | 12/2010 |
| WO | 2011/136858 | 11/2011 |
| WO | 2011/159924 | 12/2011 |
| WO | 2012/052564 | 4/2012 |
| WO | WO 2012/052564 | 4/2012 |

OTHER PUBLICATIONS

Ballentine, C. J., et al., (2002), "Production, release and transport of noble gases in the continental crust", *Reviews in Mineralogy and Geochemistry*, 47, pp. 481-538.

Ballentine, C.J., et al., (2002), "Tracing Fluid Origin, Transport and Interaction in the Crust", *Reviews in Mineralogy and Geochemistry*, 47, pp. 539-614.

Ballentine, C.J., et al., (1996), "A Magnus Opus: Helium, neon, and argon isotopes in a North Sea oilfield", *Geochemica et Cosmochimica Acta*, 60(5), 831-849.

Ballentine, C.J., et al., (1991), "Rare Gas Constraints on Hydrocarbon Accumulation, Crustal Degassing and Groundwater Flow in the Pannonian Basin", *Earth and Planetary Science Letters*, 105, pp. 229-246.

Battani, A., et al., (2010), "Trinidad Mud Volcanoes: The origin of the gas", *Shale Tectonics: AAPG Bulletin Memoir*, 93, pp. 225-238.

Bell, R. J., et al., (2007), "Calibration of an in situ membrane inlet mass spectrometer for measurements of dissolved gases and volatile organics in seawater", *Environ. Sci. Technol.* 41, pp. 8123-8128.

Bosch, A., et al., (1988), "Natural Gas Association with water and oil as depicted by atmospheric noble gases: case studies from the southeastern Mediterranean Coastal Plain", *Earth and Planetary Science Letters*, 87, 338-346.

Camilli, R., et al., (2010), "Tracking Hydrocarbon Plume Transport and Biodegradation at Deepwater Horizon", *Science* 330, pp. 201-204.

Camilli. R.C., et al., (2009), "Characterizing Spatial and Temporal Variability of Dissolved Gases in Aquatic Environments with in situ Mass Spectrometry", *Environmental Science and Technology* 43(13), pp. 5014-5021.

Camilli, R., et al. (2007), "Characterizing Marine Hydrocarbons With In-Situ Mass Spectrometry", *IEEE/MTS Oceans* (IEEE/MTS, Vancouver, Canada, 2007), pp. 1-7.

Chung, H.M., et al., (1988), "Origin of gaseous hydrocarbons in subsurface environments: theoretical considerations of carbon isotope distribution in M. Schoell (Ed.)", *Origins of Methane in the Earth. Chem. Geol.*, 71, pp. 97-103.

Crovetto, R., et al., (1982), "Solubilities of inert gases and methane in $H_2O$ and $D_2O$ in the temperature range of 300 to 600K", *Journal of Chemical Physics* 76(2), pp. 1077-1086.

Dunn-Norman, S., et al, (2004), "Reliability of Pressure Signals in Offshore Pipeline Leak Detection", *Final Report to Dept. of the Interior*, MMS TA&R Program SOL 1435-01-00-RP-31077.

Heaton, T.H.E., et al., (1981), "'Excess air' in groundwater", *Journal of Hydrology*, 50, pp. 201-216.

Hohl, D, et al., (2010), "Energy, Environment and Climate Directorate White Paper", *DCO Energy, Environment and Climate Workshop*, pp. 1-38.

Holbrook,W.S., et al., (2003), "Thermohaline fine structure in an oceanographic front from seismic reflection profiling", *Science*, v. 301, pp. 821-824.

Huc, A., (2003), "Petroleum Geochemistry At the Dawn of the 21st Century", *Oil & Gas Science and Technology—Rev. Ifp*, vol. 58, No. 2, pp. 233-241.

Kharaka, Y.K., et al., (1988), "The solubility of noble gases in crude oil at 25-100° C.", *Applied Geochemistry*, 3, pp. 137-144.

Kinsey, J.C., et al., (2011), "Assessing the deepwater horizon oil spill with the sentry autonomous underwater vehicle", *IROS'11—2011 IEEE/RSJ International Conference on Intelligent Robots and Systems: Celebrating 50 Years of Robotics*. IEEE International Conference on Intelligent Robots and Systems, pp. 261-267.

Jakuba, M.V., et al., (2011), "Toward automatic classification of chemical sensor data from autonomous underwater vehicles", *AIROS'11—2011 IEEE/RSJ International Conference on Intelligent Robots and Systems: Celebrating 50 Years of Robotics*. IEEE International Conference on Intelligent Robots and Systems, pp. 4722-4727.

Lamontagne, R.A., et al., (2001), "Response of METS Sensor to Methane Concentrations Found on the Texas-Louisiana Shelf in the Gulf of Mexico", *Naval Research Laboratory report NRL/MR/6110—01-8584*, pp. 1-13.

Larter, S.R., et al., (1995), "Reservoir geochemistry: methods, applications and opportunities", *Geological Society of London Special Publication*, 86, pp. 5-32.

Liu, W., et al. (2007), "Ternary Geochemical-Tracing System in Natural Gas Accumulation", *Science in China Series D—Earth Sciences*, vol. 50, No. 10, pp. 1494-1503.

Makris NC, et al. (2006), "Fish Population and Behavior Revealed by Instantaneous Continental Shelf-Scale Imaging", *Science*, 311, pp. 660-663.

Mangelsdorf, K., et al., (2011), "Microbial Lipid Markers Within and Adjacent to Challenger Mound in the Belgica Carbonate Mound Province, Porcupine Basin, Offshore Ireland (IODP Expedition 307)", *Marine Geology* 282, pp. 91-101.

Narr, W.M., et al., (1984), "Origin of reservoir fractures in Little Knife Field, North Dakota", *American Association of Petroleum Geologists Bulletin*, 68, pp. 1087-1100.

Ozgul, E., (2002), "Geochemical Assessment of Gaseous Hydrocarbons: Mixing of Bacterial and Thermogenic Methane in the Deep Subsurface Petroleum System, Gulf of Mexico Continental Slope", *Thesis, Texas A&M University*, pp. 1-167.

Pinti, D.L., et al., (1995), "Noble gases in crude oils from the Paris Basin: Implications for the origin of fluids and constraints on oil-was-gas-interactions", *Geochemica et Cosmochimica Acta*, 59(16), pp. 3389-3404.

Prinzhofer, A., et al. (2003), "Gas Isotopes Tracing: An Important Tool for Hydrocarbons Exploration", *Oil & Gas Science and Technology—Rev. Ifp*, vol. 58, No. 2, pp. 299-311.

Sackett, WM, (1977), "Use of Hydrocarbon Sniffing in Offshore Exploration", *Journal of Geochemical Exploration* 7, pp. 243-254.

Smith, S.P., (1985), "Noble gas solubility in water at high temperature", *EOS Transactions of the American Geophysical Union*, 66, pp. 397.

Valentine, D.L, et al., (2010), "Asphalt Volcanoes as a Potential Source of Methane to Late Pleistocene Coastal Waters", *Nature Geoscience Letters*, DOI: 10.1038/NGEO848, pp. 345-348.

Zaikowski, A., et al., (1990), "Noble gas and methane partitioning from ground water: An aid to natural gas exploration and reservoir evaluation", *Geology*, 18, pp. 72-74.

Zartman, R.E., et al., (1961), "Helium, argon, and carbon in some natural gases", *Journal of geophysical research*, 66(1), pp. 227-306.

Zhang, Y., et al., (2011), "A peak-capture algorithm used on an autonomous underwater vehicle in the 2010 Gulf of Mexico oil spill response scientific survey", *Journal of Field Robotics*, vol. 28, No. 4, pp. 484-496.

Cochran, J. R., et al., (1999), "Continuous Near-Bottom Gravity Measurements Made With a BGM-3 Gravimeter in DSV Alvin on the East Pacific Rise Crest Near 9°31'N and 9°50'N", *Journal of Geophysical Research*, vol. 104, No. B5, pp. 10,841-10,861.

Volent, Z., et al., (2007), "Kelp Forest Mapping by Use of Airborne Hyperspectral Imager", *Journal of Applied Remote Sensing*, vol. 1,011503, pp. 1-22.

\* cited by examiner

EXPLORATION METHOD AND SYSTEM FOR DETECTION OF HYDROCARBONS

CROSS REFERENCE TO RELATED APPLICATION

This application is the National Stage of International Application No. PCT/US2012/064548, that published as WO 2013/071185, filed 9 Nov. 2012, which claims the benefit of International Application No. PCT/US2012/52542, filed 27 Aug. 2012, which claims priority benefit of U.S. Provisional Patent Application 61/558,822 filed 11 Nov. 2011 entitled METHOD FOR DETERMINING THE PRESENCE AND LOCATION OF A SUBSURFACE HYDROCARBON ACCUMULATION AND THE ORIGIN OF THE ASSOCIATED HYDROCARBONS, each of which is incorporated herein by reference, in its entirety, for all purposes. This application also claims the benefit of U.S. Provisional Patent Application 61/595,394 filed 6 Feb. 2012, entitled A METHOD TO DETERMINE THE LOCATION, SIZE AND IN SITU CONDITIONS IN A HYDROCARBON RESERVOIR WITH ECOLOGY, GEOCHEMISTRY, AND COLLECTIONS OF BIOMARKERS, the entirety of which is incorporated by reference herein. This application also claims the benefit of U.S. Provisional Patent Application 61/616,813 FILED 28 Mar. 2012, entitled METHOD FOR DETERMINING THE PRESENCE AND VOLUME OF A SUBSURFACE HYDROCARBON ACCUMULATION, the entirety of which is incorporated by reference herein.

FIELD OF THE INVENTION

This invention relates generally to the field of hydrocarbon exploration. Specifically, the invention is a method for detecting hydrocarbons (e.g., oil and/or gas), which may include using remote sensing along with an underwater vehicle (UV) equipped with one or more measurement components.

BACKGROUND OF THE INVENTION

This section is intended to introduce various aspects of the art, which may be associated with exemplary embodiments of the present disclosure. This discussion is believed to assist in providing a framework to facilitate a better understanding of particular aspects of the disclosed methodologies and techniques. Accordingly, it should be understood that this section should be read in this light, and not necessarily as admissions of prior art.

Hydrocarbon reserves are becoming increasingly difficult to locate and access, as the demand for energy grows globally. Typically, various technologies are utilized to collect measurement data and then to model the location of potential hydrocarbon accumulations. The modeling may include factors, such as (1) the generation and expulsion of liquid and/or gaseous hydrocarbons from a source rock, (2) migration of hydrocarbons to an accumulation in a reservoir rock, (3) a trap and a seal to prevent significant leakage of hydrocarbons from the reservoir. The collection of these data may be beneficial in modeling potential locations for subsurface hydrocarbon accumulations.

At present, reflection seismic is the dominant technology for the identification of hydrocarbon accumulations. This technique has been successful in identifying structures that may host hydrocarbon accumulations, and may also be utilized to image the hydrocarbon fluids within subsurface accumulations as direct hydrocarbon indicators (DHIs). However, this technology may lack the required fidelity to provide accurate assessments of the presence and volume of subsurface hydrocarbon accumulations due to poor imaging of the subsurface, particularly with increasing depth where acoustic impedance contrasts that cause DHIs are greatly diminished or absent. Additionally, it is difficult to differentiate the presence and types of hydrocarbons from other fluids in the subsurface by such remote measurements.

Current geophysical, non-seismic hydrocarbon detection technologies, such as potential fields methods like gravity or magnetics or the like, provide coarse geologic subsurface controls by sensing different physical properties of rocks, but lack the fidelity to identify hydrocarbon accumulations. These tools may provide guidance on where in a basin seismic surveys should be conducted, but do not significantly improve the ability to confirm the presence of hydrocarbon seeps or subsurface hydrocarbon accumulations. Other non-seismic hydrocarbon detection technologies may include geological extrapolations of structural or stratigraphic trends that lead to prospective hydrocarbon accumulations, but cannot directly detect these hydrocarbon accumulations. Other techniques may include monitoring hydrocarbon seep locations as an indicator of subsurface hydrocarbon accumulations. However, these techniques are limited as well. For example, ssatellite and airborne imaging of sea surface slicks, and shipborne multibeam imaging followed by targeted drop core sampling, have been the principal exploration tools used to locate potential seafloor seeps of hydrocarbons as indicators of a working hydrocarbon system in exploration areas. While quite valuable, these technologies have limitations in fidelity, specificity, coverage, and cost.

As a result, an enhancement to exploration techniques that integrates various other techniques is needed. This integration of techniques may provide a pre-drill technology that determines the presence and location of thermogenic hydrocarbon seepages from the seafloor. Further, this method may be utilized to locate seafloor hydrocarbon seeps accurately and cost-effectively over the basin-to-play scale as a means to enhance basin assessment and to high-grade areas for exploration.

SUMMARY OF THE INVENTION

In one embodiment, a method for detecting hydrocarbons is described. The method includes performing a remote sensing survey of a survey location; analyzing the remote sensing data from the remote sensing survey to determine a target location; deploying an underwater vehicle (UV) into a body of water; navigating the UV within the body of water to the target location; obtaining measurement data within the body of water at the target location; determining whether hydrocarbons are present at the target location based on the measurement data.

In one or more embodiments, the method may utilize certain features related to remote sensing. For example, performing the remote sensing survey may include creating satellite imagery of the survey location or navigating an airborne vehicle to obtain an airborne survey of the survey location. Further, the remote sensing survey may include performing one or more of ocean acoustic waveguide survey; water column seismic survey; active acoustic sensing survey; imagery and spectroscopy of slicks and atmospheric gas plumes; passive acoustic sensing survey; magnetic and gravity surveys; optical sensing survey and thermal anomalies detection survey. Also, the performing the remote sensing survey may include imaging the survey location via one or more of multibeam echosounder and sub-bottom profiler via a marine surface vessel or underwater vehicle.

In one or more embodiments, the method may include certain direct measurements. For example, the method may include determining the concentration of one or more of thermogenic methane, ethane, propane, and butane, other alkanes, aromatics, or non-hydrocarbon gases (e.g., H2S, N2, CO2) from the measurement data, conducting a drop and piston core sampling technique based on the obtained measurement data within the body of water at the target location, measuring one or more of a pH concentration and an oxidation state in the body of water; and/or measuring magnetic anomalies via multicomponent magnetometers or gravity with a gravimeter. Further, the method may include obtaining biological and chemical sampling of one or more of fluids, gases, and sediments to determine depth, type, quality, volume and location of a subsurface hydrocarbon accumulation from the measurement data and/or measuring molecular and isotopic signatures of non-hydrocarbon gases and hydrocarbons in the body of water. As another example, the method may include creating one or more of a chemical map and a physical map of anomalies within the body of water to locate hydrocarbon seep vents.

BRIEF DESCRIPTION OF THE DRAWINGS

The foregoing and other advantages of the present disclosure may become apparent upon reviewing the following detailed description and drawings of non-limiting examples of embodiments.

DETAILED DESCRIPTION OF THE PREFERRED EMBODIMENTS

Figure 1:
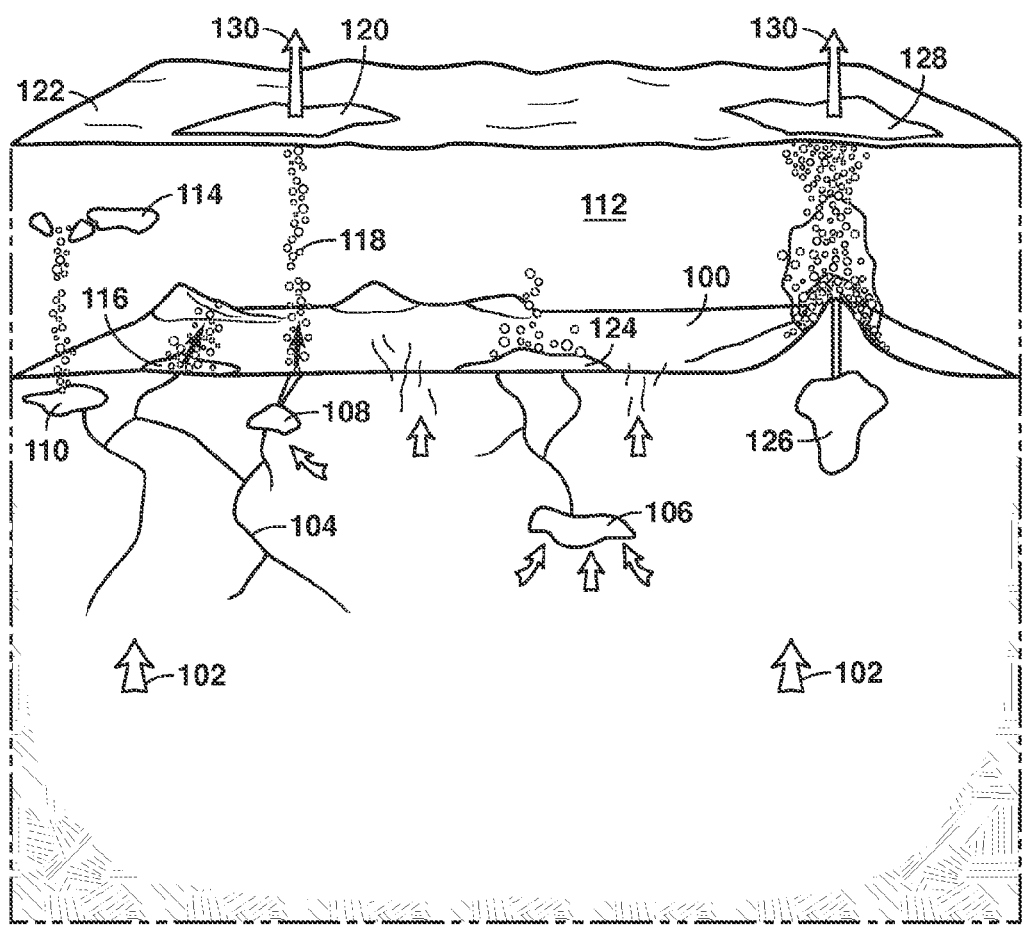
FIG. 1 is a side elevational view of a seafloor.

In the following detailed description section, the specific embodiments of the present disclosure are described in connection with preferred embodiments. However, to the extent that the following description is specific to a particular embodiment or a particular use of the present disclosure, this is intended to be for exemplary purposes only and simply provides a description of the exemplary embodiments. Accordingly, the disclosure is not limited to the specific embodiments described below, but rather, it includes all alternatives, modifications, and equivalents falling within the true spirit and scope of the appended claims.

Various terms as used herein are defined below. To the extent a term used in a claim is not defined below, it should be given the broadest definition persons in the pertinent art have given that term as reflected in at least one printed publication or issued patent.

To begin, a seep is a natural surface leak of gas and/or oil. The hydrocarbon (e.g., petroleum) reaches the surface of the Earth's crust along fractures, faults, unconformities, or bedding planes, or is exposed by surface erosion into porous rock. The presence of an oil or gas seep at the seafloor or sea surface indicates that three basic geological conditions critical to petroleum exploration have been fulfilled. First, organic-rich rocks have been deposited and preserved (source presence). Second, the source has been heated and matured (e.g., source maturity). Third, secondary migration has taken place (e.g., hydrocarbon migration from the source location). While a surface seep of thermogenic hydrocarbons does not ensure that material subsurface oil and gas accumulations exist, seeps provide a mechanism to de-risk elements of an exploration play. That is, the seep may be utilized to remove uncertainty from the modeling of the subsurface.

In the present disclosure, an enhancement to exploration techniques that integrates various other techniques is described. As hydrocarbon occurrence data is typically not easily obtained for a regional scale and not appropriately evaluated in the context of integrated hydrocarbon systems, the ability to identify and characterize seeps and thermogenic hydrocarbons in the water column provides significant enhancements for evaluating and capturing opportunities. As a result, the present techniques provide a method to locate seafloor hydrocarbon seeps accurately and cost-effectively over the play to basin scale (e.g., 1,000's to 100,000's $km^2$) as a means to enhance basin assessment and to high-grade areas for exploration. This method overcomes conventional failures in frontier hydrocarbon exploration, which are associated with the inability to fully evaluate, understand, and appropriately risk the hydrocarbon system components.

In one or more embodiments, the method utilizes a combination of satellite, airborne, acoustic and seismic techniques along with underwater sensors to characterize and map hydrocarbons in a marine environment. The combination of geophysical techniques along with underwater sensors provides a more complete characterization and mapping of hydrocarbons in the marine environment over play to basin scale exploration areas. The various independent technologies may include remote sensing (e.g., satellite and/or airborne), seismic and acoustic imaging (e.g., ship-based initially: multibeam echosounder, side-scan sonar, sub-bottom profiler; which may also be included in AUV for unsurpassed imaging due to proximity to seafloor, but much more local in scope), magnetic and gravity surveying (either from ship or air-based tools, or from AUV more locally), chemical sensing (AUV: primarily mass spectrometer and fluorometer), and sediment, biological and chemical sampling (e.g., piston cores typically, but may preferably utilize an underwater vehicle to obtain sediment, fluid (oil, water), or and/or gas samples for noble gases and isotopologues, and biology). The method may utilize airborne vehicles and marine vessels (e.g., ships and/or underwater vehicles (e.g., unmanned underwater vehicles, which may include remotely operated vehicles (ROVs) or autonomous underwater vehicles (AUVs)). When combined into an integrated method, these technologies may determine the presence and location of thermogenic hydrocarbon seepages from the seafloor to be determined.

To begin, remote sensing techniques may be utilized to determine the location of hydrocarbon seeps. Satellite and/or airborne sensing techniques are used to indicate hydrocarbon slicks that have emanated to the sea-surface from natural hydrocarbon seeps at the seafloor, thus indicating a favorable area to conduct further surveys using additional described methods. Seismic reflection imaging is used widely offshore to image sub-bottom structure and may be utilized for the determination of pore fluids in the subsurface, such as gas, oil, or water. These surveys are performed in marine vessels. Reflection seismic imaging of seeps in the water column, especially near the seafloor, due to small bulk density and temperature changes in the seep may also be possible, as suggested by references in oceanography (Holbrook W S, Paramo P, Pearse S, and Schmitt R W. 2003. Thermohaline fine structure in an oceanographic front from seismic reflection profiling, Science, v. 301, p. 821-824.). Existing 2D and 3D seismic streamer data may contain such information, but this has not been practiced. Seismic responses may include sub-horizontal perturbations in various natural internal ocean structures, such as thermocline boundaries. Internal noises at shallow depths and less structuring at large depths may confine detectible perturbations to specific ranges, such as 400 meters to 2000 meters beneath the sea surface. Regional 2D seismic data may provide evidence of such seeps, which may include useful information for evaluating hydrocarbon exploration opportunities. At lower frequencies, acoustic backscatter techniques using survey swaths of 10-100 km, being used in marine fishery studies, may be able to quickly locate macroscopic seeps over basin-scale areas greater than 100,000 $km^2$ by using the ocean thermocline as a waveguide (Makris N C, Ratilal P, Symonds D T, Jagannathan S, Lee S, Nero R W. 2006. Fish Population and Behavior Revealed by Instantaneous Continental Shelf-Scale Imaging. Science, 311:660-663). However, the efficacy for near-bottom plumes where only small bubbles may be indicative of a hydrocarbon seep is being tested. Such surveys of this kind, either stand-alone or in conjunction with other surveys at the sea surface, may be an effective basin evaluation tool.

A useful technique for imaging potential hydrocarbon seeps includes a combination of ship-based multibeam echosounder (MBES) and sub-bottom profiler (SBP). The optimum frequencies utilized in these methods is dependent on the water depth expected over the survey area. The MBES is used to obtain sea-bottom topography, roughness, and hardness, while the SBP provides subsurface information to shallow depths beneath the seafloor. Reflective surfaces at the seafloor (e.g., carbonate hardgrounds) can be associated with current microbial activity where hydrocarbons are metabolized, consistent with hydrocarbon seepage. Similarly, topographic features at the seafloor, such as pockmarks, faults, volcanoes, and salt-related depressions or positive features, locate potentially good areas for hydrocarbon migration from the subsurface to the seafloor as seeps. MBES data can also indicate density contrasts in the water column caused by bubbles emanating from the seafloor as positive indicators of potential hydrocarbon seeps. All of this information is integrated with any seismic data described above to provide targets for additional surveying to confirm the presence of hydrocarbons.

As another surveying technique, magnetic and gravity surveying may also be utilized to obtain additional information for the process. Hydrocarbon seeps can change the pH and oxidation state in the subsurface within and near the plume, and thus can form magnetic minerals, such as magnetite ($Fe_3O_4$) or greigite ($Fe_3S_4$) if sufficient Fe is present and other conditions are favorable. Weak magnetic anomalies can be formed by this process, but may be difficult to measure at the sea surface except in very shallow water. Subsea multicomponent magnetometers may be utilized in AUVs if they have the necessary sensitivity and accuracy. Broad surveys may be performed via airborne vehicles and surface marine vessels to detect geologic perturbations where subsurface hydrocarbon migration pathways may be more likely to occur, or may include collecting data in a near-seafloor environment to detect mineral formation or alteration caused by hydrocarbon seeps and microbial interactions (e.g., common microbial mats with distinctive colors) through surveying with a suitable vehicle, such as an AUV.

After potential seep locations have been indicated through the acoustic and seismic tools described, another surveying technique may include chemical sensing. The detection of thermogenic hydrocarbons emanating from seafloor seeps, either at macro- or micro-scale may be detected to confirm whether hydrocarbon seeps are present at these locations. Measuring concentrations of thermogenic methane, ethane, propane, butane, etc., near the seafloor can be performed via compact high-sensitivity mass spectrometers and laser fluorometers (for aromatic compounds generally associated with hydrocarbon liquids), which may be utilized on an underwater vehicle, such as an AUV.

As another surveying technique, an underwater vehicle may also be utilized to collect further data from a seep. The underwater vehicle may include an unmanned underwater vehicle (e.g., an AUV, remotely operated vehicle (ROV)), a manned underwater vehicle and/or one or more sensors that are towed behind a marine vessel. The underwater vehicles may include one or more sensors configured to detect chemical or physical anomalies that are indicative of hydrocarbon seeps.

Additionally, these sensors within an underwater vehicle, which may be an unmanned vehicle, can be used to map chemical or physical anomalies around a seep to locate the specific seep vent or discharge location. The seep vent location provides a favorable site for additional biological and chemical sampling of fluids, gases, and sediments to further enhance the analysis. In particular, this method may include determining the presence and estimating information, such as depth, type, quality, volume and location, about a subsurface hydrocarbon accumulation from the measured data from the underwater vehicle. In particular, the present techniques involve the use of three independent technologies: clumped isotope geochemistry, noble gas geochemistry, and microbiology, which are combined and integrated as a workflow to enhance hydrocarbon exploration success. These three methods may provide information about the depth, fluid type (oil vs. gas) and quality, and volume of subsurface hydrocarbon accumulations to be determined from the sampling and analysis of hydrocarbon seeps (e.g., offshore and/or onshore). That is, the method may integrate existing and new biological and geochemical indicators to provide insights in opportunity identification. In addition, the integration of these biological and geochemical indicators with geological/geophysical contextual knowledge should further provide enhancements to hydrocarbon opportunity identification. These other techniques are described in U.S. Patent No. 61/595,394; U.S. Patent No. 61/616,813; U.S. Patent No. 61/558,822, which are each incorporated herein in its entirety.

In one embodiment, the present techniques involve one or more of microbial genomics; noble gas geochemistry and clumped isotope geochemistry of hydrocarbon phases. These techniques may be utilized to determine and/or estimate the presence and information, such as volume, depth, type, quality, and location of the subsurface hydrocarbon accumulation.

The microbial genomics may be utilized to provide information on the metabolic processes of subsurface microbial communities linked with those microbes sampled within sea-bottom seeps. This microbial genomics information provides an indication as to the presence of a subsurface accumulation and provides an estimation of its location (e.g., depth) based on biologic temperature ranges. This aspect relies upon the transport microbes from deep to shallow habitats to a hydrocarbon seep from subsurface hydrocarbon accumulations. This process may explain, for example, the presence of "displaced" thermophiles (microbes that live in high temperature environments) in arctic environments where crude oil is potentially degraded by anaerobic microbes, thus supporting a connection to a deeper hydrocarbon/sediment source. Different areas of hydrocarbon seepage may have different microbial anomalies relative to normal marine conditions, depending on subsurface reservoir conditions. An understanding of the metabolic processes of subsurface microbial communities linked with those microbes sampled within seabottom seeps should allow the presence of a subsurface accumulation to be detected and allow an estimation of its location (depth) based on biologic temperature ranges.

As an example, one embodiment may include a method of identifying a hydrocarbon system. In this method, a sample from an area of interest is obtained. Then, a first plurality of analyses is used to determine a community structure of an ecology of the sample and a second plurality of analyses is used to determine a community function of the ecology of the sample. The community structure and the community function are used to determine whether the ecology of the sample matches a characteristic ecology of a hydrocarbon system. When the ecology of the sample matches the characteristic ecology, the sample is identified as part of the hydrocarbon system. This aspect is further described in U.S. Patent No. 61/595,394, which is incorporated herein in its entirety.

With regard to the noble gas geochemistry, the noble gases (He, Ne, Ar, Kr, Xe) are conservative elements that do not generally participate in chemical reactions. The concentrations of noble gases in oil, gas, and water are based on the combined influence of their solubilities, which are a function of pressure, temperature, and fluid composition (P-T-X) that prevailed during dissolution or exsolution, interaction and mixing with other fluids, and the ingrowth of noble gases from the radioactive decay of crustal minerals. If the water PTX conditions in contact with a subsurface hydrocarbon accumulation can be estimated or measured, the hydrocarbon accumulation size can be estimated or calculated based on the solubility partitioning of noble gases between water and hydrocarbons. An atmospherically uncontaminated hydrocarbon seep sample analyzed for noble gases along with estimated water PTX conditions, should allow an accumulation size (hydrocarbon/water ratio) to be estimated.

As an example, one embodiment may include a method for determining the presence, type, quality and/or volume of a subsurface hydrocarbon accumulation from a sample related thereto. An initial concentration of atmospheric noble gases present in formation water in contact with the subsurface hydrocarbon accumulation is measured or modeled. The modeled initial concentration is modified by accounting for ingrowth of radiogenic noble gases during residence time of the formation water. A sample related to the subsurface hydrocarbon accumulation is obtained. Concentrations and isotopic ratios of noble gases present in the sample are measured. The measured concentrations and isotopic ratios of the atmospheric noble gases and the radiogenic noble gases present in the sample are compared to the measured/modified modeled concentrations of the formation water for a plurality of exchange processes. A source of hydrocarbons present in the sample is determined. An atmospheric noble gas signature measured in the hydrocarbon phase is compared with the measured/modified modeled concentration of the atmospheric noble gases in the formation water for the plurality of exchange processes. At least one of a type of hydrocarbons in the subsurface accumulation, a quality of hydrocarbons in the subsurface accumulation, a hydrocarbon/water volume ratio in the subsurface accumulation prior to escape to the surface, and a volume of the subsurface accumulation is determined.

In another aspect, a method is disclosed for determining a presence, type, quality and volume of a subsurface hydrocarbon accumulation based on analysis of a sample related thereto. The sample is analyzed to determine a geochemical signature of the sample. An initial concentration of atmospheric noble gases present in formation water in contact with the subsurface hydrocarbon accumulation is determined Ingrowth of radiogenic noble gases is modeled to modify the initial concentration for given formation water residence times. A residence time of the formation water is determined. An extent of interaction with a hydrocarbon phase is determined. The origin of the sample is determined. At least one of a type, quality and hydrocarbon/water volume ratio when the origin of the sample is a hydrocarbon accumulation is determined. From the hydrocarbon/water volume ratio, the volume of the hydrocarbon accumulation is determined.

In another aspect, a method is disclosed for determining a presence, type, quality and volume of a subsurface hydrocarbon accumulation from a hydrocarbon sample thereof. An initial concentration of atmospheric noble gases present alongside a hydrocarbon species is determined A range of expected concentrations of atmospheric and radiogenic noble gases present in the sample is modeled for a range of residence times and for various extents of interaction between formation water and a hydrocarbon phase. Concentrations and isotopic ratios of noble gases present in the sample are measured. The measured noble gas concentrations are compared with the modeled range of expected concentrations of atmospheric and radiogenic noble gases. Using the comparison it is determined whether the hydrocarbons present in the sample have escaped from the subsurface accumulation. From the measured noble gas concentrations and the modeled range of expected concentrations of atmospheric and radiogenic noble gases, the type and quality of hydrocarbons in the subsurface accumulation and the hydrocarbon/formation water volume ratio of the subsurface accumulation are estimated. The estimated type and quality of hydrocarbons in the subsurface accumulation and the hydrocarbon/formation water volume ratio of the subsurface accumulation are integrated with seismic reflection constraints on a volume of the hydrocarbon accumulation and a volume of water present in the hydrocarbon accumulation, thereby determining the volume of hydrocarbons present in the subsurface accumulation.

In still another aspect, a system is disclosed for determining a presence, type, quality and volume of a subsurface hydrocarbon accumulation from a hydrocarbon sample thereof. The system includes a processor and a tangible, machine-readable storage medium that stores machine-readable instructions for execution by the processor. The machine-readable instructions include code for determining expected concentrations of noble gases present in formation waters, code for modeling one or more exchange and fractionation processes in the expected concentrations of noble gases present in the sample, code for measuring concentrations of noble gases present in the sample, code for comparing the measured concentrations of noble gases with the modeled concentrations of noble gases in the formation waters, code for determining, using said comparison, the type and quality of hydrocarbons present in the subsurface, and code for determining whether hydrocarbons present in the sample originate directly from a source rock or whether the hydrocarbons present in the sample have escaped from a subsurface accumulation.

In still another aspect, a computer program product having computer executable logic recorded on a tangible, machine readable medium, the computer program product comprising: code for determining expected concentrations of noble gases present in formation waters, code for modeling one or more exchange and fractionation processes in the expected concentrations of noble gases present in a hydrocarbon sample taken from a hydrocarbon seep, code for measuring concentrations of noble gases present in the hydrocarbon sample, code for comparing the measured concentrations of noble gases with the modeled concentrations of noble gases in the formation waters, code for determining, using said comparison, a type and a quality of hydrocarbons present in the hydrocarbon sample, and code for determining whether hydrocarbons present in the hydrocarbon sample originate directly from a source rock or whether the hydrocarbons present in the sample have escaped from a subsurface accumulation.

In yet another aspect, a method of producing hydrocarbons, comprising: determining a presence, type, quality and/or volume of a subsurface hydrocarbon accumulation from a hydrocarbon sample thereof, wherein the determining includes modeling an initial concentration of atmospheric noble gases present in formation water in contact with a subsurface hydrocarbon accumulation, modifying the modeled initial concentration by accounting for ingrowth of radiogenic noble gases during residence time of the formation water, obtaining a hydrocarbon sample, measuring concentrations and isotopic ratios of atmospheric, mantle derived and radiogenic noble gases present in the hydrocarbon sample, comparing the measured concentrations and isotopic ratios of the atmospheric noble gases and the radiogenic noble gases present in the hydrocarbon sample to the modified modeled concentrations of the formation water for a plurality of exchange processes, determining a source of hydrocarbons present in the hydrocarbon sample, comparing an atmospheric noble gas signature measured in the hydrocarbon phase with the modified modeled concentration of the atmospheric noble gases in the formation water for a plurality of exchange processes, determining at least one of a type of hydrocarbons in the subsurface accumulation, a quality of hydrocarbons in the subsurface accumulation, a hydrocarbon/water volume ratio in the subsurface accumulation prior to escape to the surface, and a volume of the subsurface accumulation; and producing hydrocarbons using at least one of the determined type, quality, volume ratio, and volume of the subsurface accumulation. This aspect is further described in U.S. Patent No. 61/616,813, which is incorporated herein in its entirety.

A hydrocarbon compound contains atoms of carbon and hydrogen, and will be present as a natural stable isotope of carbon ($12C$, $13C$) or hydrogen ($1H$, or $2H$ often termed deuterium or D). $12C$ forms 98.93% of the carbon on Earth, while $13C$ forms the remaining 1.07%. Similarly, the isotopic abundance of $1H$ on earth is 99.985% while $2H$ has an abundance of 0.015%. Isotopologues are compounds with the same chemical formula, but differ in their molecular mass based on which isotopes are present in the molecule (e.g. $13C1H3D$ or $12C1H4$). Clumped isotopes are isotopologues in which two or more rare isotopes are present in close proximity (i.e., isotopic 'clumps'), and for which the molecular ordering of isotopes is as important as their total abundance. These rare species have distinctive thermodynamic stabilities and rates of reaction with specific fractionations during diffusion and mixing, and are far more diverse than the singly-substituted species that are the focus of established branches of isotope geochemistry. Common volatile hydrocarbons have large numbers of stable isotopologues (e.g., methane has 10; ethane has 21; propane has 36). Measurements of a single gas species could, in principle, yield two or more mutually independent thermometers that could indicate the "residence" temperature of hydrocarbons within a subsurface accumulation, in effect determining the depth location of a potential exploration target from a seep sample.

As an example, one embodiment may include a method of determining a presence and location of a subsurface hydrocarbon accumulation from a sample of naturally occurring substance. According to the method, an expected concentration of isotopologues of a hydrocarbon species is determined. An expected temperature dependence of isotopologues present in the sample is modeled using high-level ab initio calculations. A signature of the isotopologues present in the sample is measured. The signature is compared with the expected concentration of isotopologues. Using the comparison, it is determined whether hydrocarbons present in the sample originate directly from a source rock or whether the hydrocarbons present in the sample have escaped from a subsurface accumulation. The current equilibrium storage temperature of the hydrocarbon species in the subsurface accumulation prior to escape to the surface is determined A location of the subsurface accumulation is determined.

Also according to disclosed methodologies and techniques, a method of determining a presence and location of a subsurface hydrocarbon accumulation is provided. According to the method, a hydrocarbon sample is obtained from a seep. The hydrocarbon sample is analyzed to determine its geochemical signature. The analyzing includes measuring a distribution of isotopologues for a hydrocarbon species present in the hydrocarbon sample. A stochastic distribution of the isotopologues for the hydrocarbon species is determined A deviation of the measured distribution of isotopologues from the stochastic distribution of the isotopologues for the hydrocarbon species is determined. The origin of the hydrocarbon sample is determined. A storage temperature of the hydrocarbon species is determined when the origin of the hydrocarbon sample is a hydrocarbon accumulation. From the storage temperature, the location of the hydrocarbon accumulation is determined.

According to methodologies and techniques disclosed herein, a method is provided for determining a presence of a subsurface hydrocarbon accumulation from a sample of naturally occurring substance. According to the method, an expected concentration of isotopologues of a hydrocarbon species is determined. An expected temperature dependence of isotopologues present in the sample is modeled using high-level ab initio calculations. A clumped isotopic signature of the isotopologues present in the sample is measured. The clumped isotopic signature is compared with the expected concentration of isotopologues. It is determined, using the comparison, whether the hydrocarbons present in the sample have escaped from a subsurface accumulation, thereby determining a presence of the subsurface accumulation.

According to disclosed methodologies and techniques, A computer system is provided that is configured to determine a presence and location of a subsurface hydrocarbon accumulation from a sample of naturally occurring substance. The computer system includes a processor and a tangible, machine-readable storage medium that stores machine-readable instructions for execution by the processor. The machine-readable instructions include: code for determining an expected concentration of isotopologues of a hydrocarbon species; code for modeling, using high-level ab initio calculations, an expected temperature dependence of isotopologues present in the sample; code for measuring a clumped isotopic signature of the isotopologues present in the sample; code for comparing the clumped isotopic signature with the expected concentration of isotopologues; and code for determining, using said comparison, whether hydrocarbons present in the sample originate directly from a source rock or whether the hydrocarbons present in the sample have escaped from a subsurface accumulation.

According to still more disclosed methodologies and techniques, a method of determining a presence and location of a subsurface hydrocarbon accumulation and the origin of associated hydrocarbons collected from a surface seep is provided. According to the method, molecular modeling is integrated to determine the expected concentration of isotopologues from a hydrocarbon species of interest. A concentration of the isotopologues of the hydrocarbon species of interest is measured. Statistical regression analysis is conducted to converge on a temperature-dependent equilibrium constant and an isotopic signature unique to the absolute concentrations measured for multiple co-existing isotopologues. For the hydrocarbons collected from the surface seep, at least one of storage temperature, a source facies, and thermal maturity of source rock associated therewith is determined. This aspect is further described in U.S. Patent No. 61/558,822, which is incorporated herein in its entirety.

Beneficially, this integrated method provides a pre-drill technology that may determine the presence and location of thermogenic hydrocarbon seepages from the seafloor. Further, this method may be utilized to locate seafloor hydrocarbon seeps accurately and cost-effectively over the basin-to-play scale as a means to enhance basin assessment and to high-grade areas for exploration. The analysis of seismic and acoustic data from surface surveys, plus integrated interpretation of geophysical and chemical data from underwater vehicles, provides an enhanced method to locate seafloor seeps of thermogenic hydrocarbons cost-effectively over large areas. Further, this process provides the ability to detect the presence, volume, depth, and fluid type/quality of subsurface hydrocarbon accumulations, which is useful in hydrocarbon (HC) resource exploration in frontier and play extension settings. As a result, this process provides geoscientists with an enhanced identification technique for hydrocarbon accumulations, while having a greater confidence in the identified hydrocarbon accumulations. Various aspects of the present techniques are described further in FIGS. 1 to 5.

FIG. 1 is a diagram illustrating the numerous subsurface sources and migration pathways of hydrocarbons present at or escaping from seeps on the ocean floor 100. Hydrocarbons 102 generated at source rock (not shown) migrate upward through faults and fractures 104. The migrating hydrocarbons may be trapped in reservoir rock and form a hydrocarbon accumulation, such as a gas 106, oil and gas 108, or a gas hydrate accumulation 110. Hydrocarbons seeping from the gas hydrate accumulation may dissolve into methane and higher hydrocarbons (e.g., ethane, propane) in the ocean 112 as shown at 114, or may remain as a gas hydrate on the ocean floor 100 as shown at 116. Alternatively, oil or gas from oil/gas reservoir 108 may seep into the ocean, as shown at 118, and form an oil slick 120 on the ocean surface 122. A bacterial mat 124 may form at a gas seep location, leaking from gas reservoir 106, and may generate biogenic hydrocarbon gases while degrading thermogenic wet gas. Still another process of hydrocarbon seepage is via a mud volcano 126, which can form an oil slick 128 on the ocean surface. Oil slicks 120 and 128 or methane (and e.g., ethane, propane, etc.) gas 130 emitted therefrom are signs of hydrocarbon seepage that are, in turn, signs of possible subsurface hydrocarbon accumulation. The signatures measured from each of these seeps may be analyzed according to disclosed methodologies and techniques herein to discriminate between the different origins of hydrocarbons encountered at these seeps. In particular, methodologies and techniques disclosed herein may discriminate between hydrocarbons that have migrated directly to the surface without encountering a trap within which they can be accumulated (e.g., a first source) and hydrocarbons that have leaked from a subsurface accumulation (e.g., a second source). If the presence and volume of such a hydrocarbon accumulation can be identified, it is possible the hydrocarbons from such an accumulation can be extracted.

Figure 2:
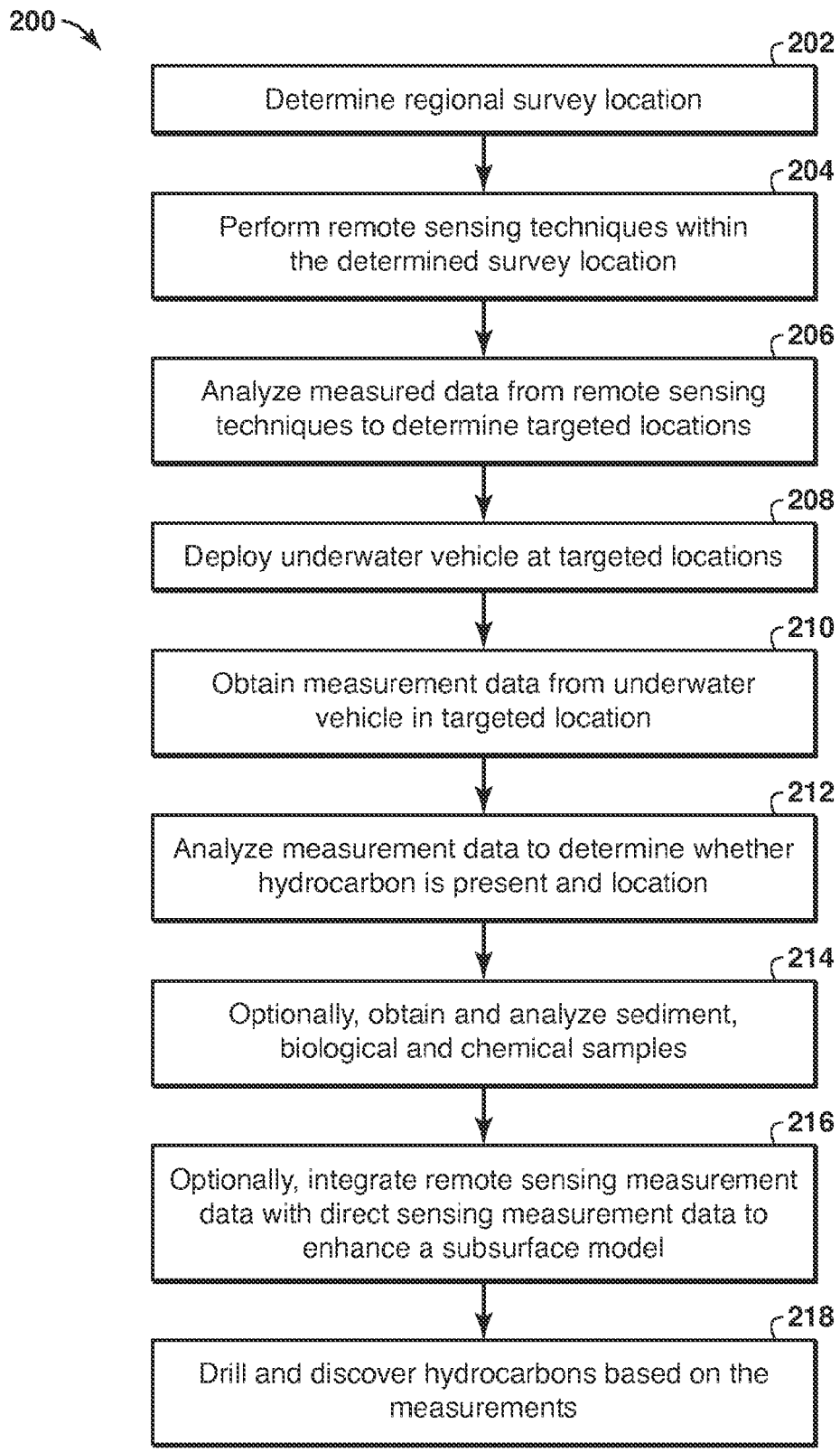
FIG. 2 is a flow chart for using remote sensing along with an underwater vehicle(s) to perform hydrocarbon exploration in accordance with an exemplary embodiment of the present techniques.

FIG. 2 is a flow chart 200 for using remote sensing along with an underwater vehicle (UV) to perform hydrocarbon exploration in accordance with an exemplary embodiment of the present techniques. In this flow chart 200, various blocks relate to performing remote sensing on a survey location, such as blocks 202 to 206, which may be referred to as a remote sensing stage. Other blocks involve the more direct measurements, which involve the operation of an underwater vehicle, such as blocks 208 to 216, which may be referred to as a direct sensing stage. Finally, block 218 relates to the use of the measured data for hydrocarbon discovery, which may be referred to as a discovery stage.

The remote sensing stage is described in blocks 202 to 206. At block 202, a regional survey location is determined. In the exploration process, offshore regions or large areas that may have hydrocarbon potential are sometimes offered or awarded by various governments to companies for exploration purposes. Within these regions that may include sizes exceeding 100,000 km$^2$, it is useful for companies to quickly and cost-effectively determine whether the region has the potential to yield hydrocarbon accumulations (i.e., evidence within the region for an active hydrocarbon system) and, if so, to locate and focus on areas within the region that have the best exploration potential. Once the regional survey location is identified, remote sensing may be performed in the identified survey location, as shown in block 204. The remote sensing survey may include satellite imagery and airborne surveys along with water column surveys, as well. The remote sensing techniques may include the ocean acoustic waveguide; water column seismic; active acoustic sensing (multibeam echo sounder, two dimensional (2D) seismic, three dimensional (3D) seismic, sub-bottom profiler, side scan sonar, etc.); imagery and spectroscopy of slicks and atmospheric gas plumes (e.g., infrared (IR) to detect atmospheric gases, radar reflectivity, etc.); towed chemical sensors (mass spectrometer, etc.); passive acoustic sensing; discrete sampling from surface vessel of air, water, or soil at various locations; drop and piston cores; magnetic and gravity surveys; optical sensing; thermal anomalies detection; and/or any other remote sensing technique. These remote sensing techniques may be performed via satellites, airborne vessels, and/or marine vessels. Concurrently with collection of the remote sensing data or after the remote sensing measurement data is collected, the measured data from the remote sensing techniques may be analyzed to determine targeted locations, as shown in block 206. An example may include interpreting multibeam echosounder and sub-bottom profiler data acquired via a marine vessel. The multibeam backscatter data may be examined for anomalous sea-bottom hardness, roughness, and/or volumetric heterogeneity in the shallow sub-bottom and by examining the bathymetry data collected for local highs, lows, fault lines, and other geologic indicators that may be consistent with permeable pathways for hydrocarbon migration to the seafloor. In other words, these remote sensing methods provide targets for possible hydrocarbon seep locations. Similarly, if any slick data from previous satellite imagery interpretations are available or seismic data, etc. are available, that information may be integrated with the multibeam and sub-bottom profiler data to improve or "high-grade" the best locations for possible hydrocarbon seeps. Additionally, interpretations made from these results, preferable with the availability of seismic information, may allow geologic interpretations or models to be constructed about possible hydrocarbon "plays" or prospects, based on this initial information. These potential areas may again be useful targets to determine whether thermogenic hydrocarbons are present as seeps.

The direct measurements in the direct sensing stage, which involve the operation of an underwater vehicle, are described further in blocks 208 to 216. At block 208, the underwater vehicle is deployed at the target location. The deployment may include transporting the underwater vehicle to the target location, which may be one of various target locations identified from the remote sensing survey. The underwater vehicle may be transported via another marine vessel and/or airborne vessel to the desired target location. The deployment may also include configuring the underwater vehicle to obtain certain measurements and/or to follow a certain search pattern. As may be appreciated, the configuration of the underwater vehicle may be performed prior to the transporting of the underwater vehicle to the target location, at least partially during the transporting of the underwater vehicle and/or at least partially at the target location. Regardless, the configuration of the underwater vehicle may include determining a sequence of operations to be performed by the underwater vehicle to perform the direct measurement survey at the target location. For instance, this configuring the underwater vehicle may include programming the navigation components to follow a general path, adjusting operational parameters and/or settings, adjusting the configuration of the monitoring components, and/or other suitable operational adjustments. This may also include inserting certain equipment (e.g., certain monitoring components) into the underwater vehicle for use in monitoring. Once configured, the underwater vehicle may be deployed into the body of water, which may include launching the underwater vehicle, and initiating underwater vehicle measurement operations. As an example, the deployment may include lowering the underwater vehicle from the deck of a marine vessel into the body of water or dropping the underwater vehicle into the body of water. The initiation of the measuring may be performed on the vessel or once the underwater vehicle is disposed in the body of water.

The operation of the underwater vehicle is described in blocks 210. As may be appreciated, the operation of the underwater vehicle, which may be an AUV, may include various processes that repeat during an operational period (e.g., period of time that the underwater vehicle is measuring data). During this operational period, the underwater vehicle may navigate toward targeted locations or may obtain measurements along a specific search pattern. To navigate, the underwater vehicle may utilize navigation components, which may include one or more propulsion components, one or more steering components and the like. The one or more propulsion components may include a motor coupled to one or more batteries and coupled to a propeller assembly, via a shaft, for example, as is known in the art. The propeller assembly may be utilized to move fluid in a manner to move the underwater vehicle relative to the body of water. The navigation components may utilize sensors or other monitoring devices to obtain navigation data. The navigation data may include different types of navigational information, such as inertial motion unit (IMU), global positioning system information, compass information, depth sensor information, obstacle detection information, SONAR information, propeller speed information, seafloor map information, and/or other information associated with the navigation of the underwater vehicle.

The underwater vehicle may obtain measurements within the target location. For example, the underwater vehicle may utilize the measurement components, such as one or more modules to receive measurement data and a process control unit to manage the received data, calculate operational and measurement parameters from the received data, determine adjustments to the operation of the underwater vehicle and determine if additional measurement information should be obtained. The measurement components may include fluorescence polarization components, fluorometric components, wireless component (e.g., acoustic components and/or SONAR components), methane or other chemical compound detection components, temperature components, camera components and/or other measurement components. The measurement data may include camera images, SONAR data and/or images, acoustic data, temperature data, mass spectrometric data, conductivity data, fluorometric data, and/or polarization data, for example. The data can be in the format of images, raw data with specific format for the component, text files, and/or any combination of the different types. The underwater vehicle may include integrated sensor payloads that are utilized to monitor a large area, while two or more AUVs, which may communicate between each other, may also be utilized in other applications to monitor other areas that may be smaller in extent. Other sensors may include functionality to provide chemical specificity of applied sensors (e.g., underwater mass spectrometry). These sensors may discriminate thermogenic hydrocarbons, which may be preferred, from biogenic hydrocarbons and may determine whether the seep is associated with gas, oil, or a combination of gas and oil. As an example, the underwater vehicle may be an AUV. The AUV may include artificial intelligence that is configured to detect and navigate toward peak concentrations of targeted chemicals, such as propane, and data reporting is done periodically to a small surface vessel or to shore using satellite links.

Once the measurement data is obtained, it may be analyzed to determine whether hydrocarbons are present and their location, as shown in block 212. As the measurement data may include various forms, the measurement data may be analyzed on the underwater vehicle via the respective measurement equipment and/or transmitted to another location for processing. Certain of these aspects are discussed below.

At block 214, the sediment, biological and chemical samples may be obtained and analyzed to further enhance the process. Sediment samples may be acquired by ship-based drop or piston core surveys, based on the integration of the remote sensing and direct measurement information (e.g., sub-bottom profile and seismic data linked to seep locations), which may greatly improve the ability to collect meaningful sediment samples that contain hydrocarbons. These samples are then analyzed (which may be in a laboratory or onboard a vehicle) using fluorometry, gas chromatography (GC), and more sophisticated GC-MS (mass spectrometry)-MS or GC-GC time of flight mass spectrometry or additional techniques to obtain biomarkers and other indicators of hydrocarbon source facies and thermal maturity. The samples may also be obtained via underwater vehicle. In particular, this method may include determining the presence and estimating information, such as depth, type, quality, volume and location, about a subsurface hydrocarbon accumulation from the measured data from the samples acquired by the underwater vehicle. The samples may be subjected to three independent analysis technologies, such as clumped isotope geochemistry, noble gas geochemistry, and microbiology. These may each be utilized to provide additional information about the depth, fluid type (oil vs. gas) and quality, and volume of subsurface hydrocarbon accumulations. That is, the method may integrate existing and new biological and geochemical indicators to provide insights in opportunity identification. In addition, the integration of these biological and geochemical indicators with geological/geophysical contextual knowledge with the other geological and measurement data further provides enhancements to hydrocarbon opportunity identification. These analysis techniques are described in U.S. Patent No. 61/595,394; U.S. Patent No. 61/616,813; and U.S. Patent No. 61/558,822.

The remote sensing measurement data may be integrated with the direct sensing data to enhance a subsurface model, as shown in block 216. As an example, the measured data may be organized with the location of the underwater vehicle or a location to correlate the measured data with other surveys of the subsurface geology. As a specific example, multi-beam echo sounding data may be associated with the location of a surface vehicle and used to detect sea bottom topography, texture, and density, and SBP (sub-bottom profiler) to locate shallow subsurface gas anomalies and hydrate layers associated with bottom simulating reflectors. The measured data from chemical sensors associated with an underwater vehicle may be used to locate anomalous chemistries associated with seeps and seep vents, to map these anomalies relative to geologic features, and to distinguish thermogenic from biogenic gas, and gas from oil. These different types of data may be integrated based on location information associated with the respective data to provide additional information. Chemical results from drop or piston core surveys are further integrated with seismic, gravity, and magnetic data that have been combined to create subsurface models of the geology and hydrocarbon system in a region. The subsurface models are further enhanced by the results of microbial ecology, clumped isotopes, and noble gas signatures from samples acquired by an underwater vehicle.

Finally, block 218 relates to the designation of a drilling location for discovery of hydrocarbons based on the measured data. The discovery of hydrocarbons is based on a determination that is made whether to access hydrocarbons from the target locations based at least partially on the measured data or the integrated data. The determination may include analyzing the measured data for one or more of the hydrocarbon accumulation type, quality, depth and volume obtained from the microbial ecology, clumped isotope and noble gas signatures and/or these data integrated with the geological and geophysical data. The discovery of the hydrocarbons involves drilling a well to provide access to the hydrocarbon accumulation. Further, the production may include installing a production facility is configured to monitor and produce hydrocarbons from the production intervals that provide access to the subsurface formation. The production facility may include one or more units to process and manage the flow of production fluids, such as hydrocarbons and/or water, from the formation. To access the production intervals, the production facility may be coupled to a tree and various control valves via a control umbilical, production tubing for passing fluids from the tree to the production facility, control tubing for hydraulic or electrical devices, and a control cable for communicating with other devices within the wellbore.

Beneficially, this integrated method provides an enhancement in the exploration of hydrocarbons. In particular, the method may be utilized prior to drilling operations to reduce exploration risk by providing more information about the presence and location of thermogenic hydrocarbon seepages from the seafloor. As a result, this method provides a cost-effective technique to enhance basin assessment and to high-grade areas for exploration. The analysis of seismic, gravity, magnetics, and acoustic data from surface surveys, plus integrated interpretation of physical and chemical data from underwater vehicles, provides an enhanced method to locate seafloor seeps of thermogenic hydrocarbons cost-effectively over large areas.

Further, mapping of anomalies around hydrocarbon seeps may be useful to locate areas where fluids are exiting the subsurface onto the seafloor. This approach may be utilized to enhance other technologies, such as drop core sampling of hydrocarbon-associated sediments, or the acquisition of fluids or gases above, at, or under the seafloor. Accordingly, this integrated method may be utilized to further enhance the exploration activities.

Figure 3:
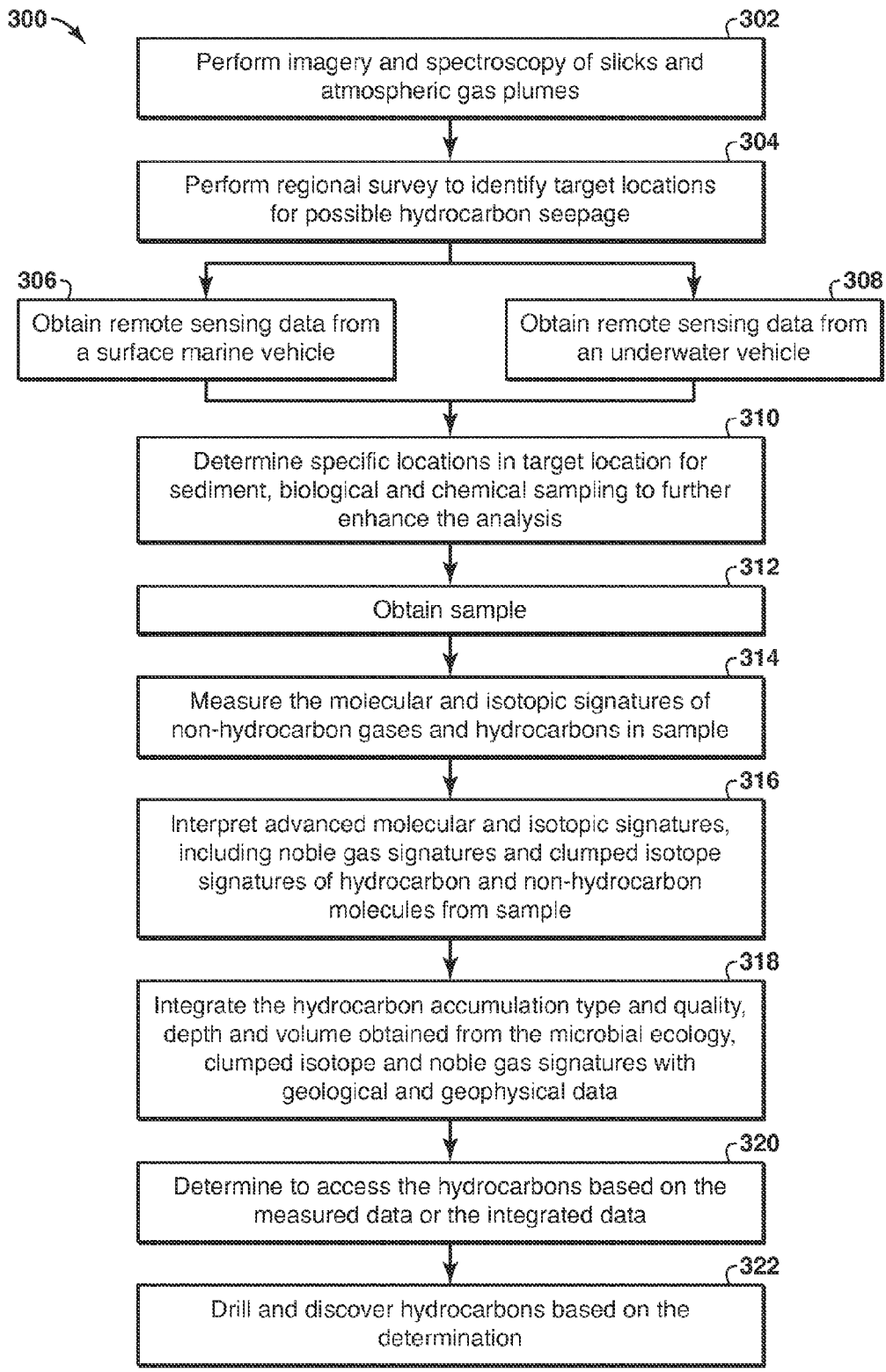
FIG. 3 is a flow chart for using remote sensing along with underwater vehicle (UV) to perform hydrocarbon exploration in accordance with another exemplary embodiment of the present techniques.

As another specific embodiment, FIG. 3 is a flow chart 300 for using remote sensing along with an underwater vehicle (UV) to perform hydrocarbon exploration in accordance with another exemplary embodiment of the present techniques. In this flow chart 300, various blocks relate to the remote sensing stage, direct sensing stage and discovery stage, as noted above in FIG. 2, and are utilized to determine the location of a hydrocarbon seep. In this flow chart 300, the remote sensing stage may include blocks 302 to 310, the direct sensing stage may include blocks 312 to 318 and the discovery stage may include blocks 320 to 322.

The remote sensing stage is described in blocks 302 to 310. At block 302, imagery and spectroscopy of slicks and atmospheric gas plumes is performed. For example, these tools may include high resolution satellite, radar (e.g., synthetic aperature radar) and ultra-violet imagers that can detect the presence and geographic extent of oil slicks. Multi-spectral imaging data can also be used to map large oil-slicks that occur offshore. As another example, infrared sensing may be utilized to detect atmospheric gases, radar reflectivity; and/or airborne surveys. Then, at block 304, a regional survey location may be utilized to identify one or more target location within the region. This determination may include identifying a region that has potential to include one or more hydrocarbon seeps based on the imagery and spectroscopy data.

Once the regional survey location is identified, the remote sensing may be performed via a marine vessel, as shown in block 306, and via the underwater vehicle, as shown in block 308. At block 306, remote sensing data is obtained from a surface marine vehicle, such as a surface vessel. The remote sensing data from the surface vessel may include performing active acoustic sensing (e.g., multibeam echo sounder, 2D seismic, 3D seismic, sub-bottom profiler, side scan sonar, etc.), chemical analysis (e.g., towing in situ chemical sensors (mass spectrometer, etc.)); discrete in situ sampling from surface vessel of air, water, or soil at various locations; drop or piston cores, sampling system; pumping liquid to sensing location, passive acoustic techniques; magnetic and gravity surveys; optical sensing (remote or in situ); thermal anomalies analysis; any other remote or in situ sensing technique. At block 308, the remote sensing data from the underwater vehicle (e.g., underwater deployment device (AUV, ROV, floats, any other underwater deployment device); may include analyzing of sediment or water samples. Then, at block 310, the specific locations for sediment, biological and chemical sampling (e.g., target location) are determined to further enhance the analysis. This determination may include identifying target locations for focused investigations of points of interest to confirm presence of thermogenic hydrocarbon seepage (e.g., molecular geochemistry of seafloor sediments, water column, etc.).

The biological and chemical sampling in the direct sensing stage is performed at blocks 312 to 318. The sample is obtained in block 312. The location of the hydrocarbon sample may be based on a known seep location or determining a seep location through known techniques. The one or more samples are obtained from the hydrocarbon sample location. If the hydrocarbon location is a seep, the sampling of seep locations may include (i) confirming the presence of hydrocarbons (e.g., biogenic, thermogenic, abiogenic) at the seep location and (ii) conducting advanced biological and geochemical analysis after appropriate sampling. The sampling methods used to collect the samples of interest may include gravity or piston drop core sampling, the use of manned submersibles, autonomous underwater vehicles (AUV) or remotely operated vehicles (ROV) with coring sampling devices, and gas sampling apparatus. Sampling may also include collection of surface sediments surrounding the seep location and collection of fluids from within the seep conduit. A sample can comprise (i) any surface sample, such as a sediment sample taken from the sea-floor or a sample of seeped fluids, (ii) any sample taken from the water column above a seep location, m or (iii) any sample taken from within the seep conduits below the surface. Identification of the presence of hydrocarbons may be determined by standard geochemical analysis. This may include but is not restricted to maximum fluorescence intensity and standard molecular geochemistry techniques such as gas chromatography (GC). For biology samples, appropriate preservation should be taken, as is known in the art. Similarly, gas and/or oil samples that are subjected to clumped isotope and noble gas analysis may be collected using funnels or inserted into seep conduits connected to sampling cylinders.

After the sample obtaining stage, the molecular and isotopic signatures of non-hydrocarbon gases and hydrocarbons in the sample are measured, as shown in block 314. In particular, the molecular and isotopic signatures of non-hydrocarbon gases (e.g. $H_2S$, $CO_2$, $N_2$) and hydrocarbons are measured, which includes the analysis of noble gas signatures (He, Ne, Ar, Kr and Xe) and the isotopologue or clumped isotope signature of both non-hydrocarbon and hydrocarbon molecules (in gases, water, and/or oils). Isotopologues are molecules that differ only in their isotopic composition. Clumped isotopes are isotopologues that contain two or more rare isotopes. The sample of interest may comprise water, oil, natural gas, sediments or other types of rocks, or fluids present in sediments, rocks, water or air. Measurement of the abundance of each noble gas isotope can be conducted following standard extraction techniques using mass spectrometry. Measurement of the abundance of each clumped isotope or isotopologue can be conducted using multiple techniques, such as mass spectrometry and/or laser-based spectroscopy. The ecology of samples (e.g., sediment, seawater, seeped fluids and the like) can be characterized through a number of different techniques. These may include but are not restricted to deoxyribonucleic acid (DNA) analysis, ribonucleic acid (RNA) analysis, (meta) genomics, (meta) proteomics, (meta) transcriptomics, lipid analysis, and culture-based methods. The analysis may include both (semi) quantitative (e.g., qPCR (quantitative polymerase chain reaction), next-generation sequencing) and qualitative assessments (e.g., sequencing, microscopy, phenotype tests). Standard molecular analysis is conducted to characterize the organic signature of hydrocarbons extracted from the sample. Analysis may include the use of gas chromatography-mass spectrometry (GC/MS), GC/GC/MS, and liquid chromatography. Inorganic analysis of samples may also be conducted. Analysis may include but is not restricted to inductively coupled plasma mass spectrometry (ICP-MS) and ICP-optical emission spectroscopy. Gas chemistry analysis may also be conducted and may include isotope ratio-mass spectrometry and GC.

At block 316, the interpretation of advanced molecular and isotopic signatures, including noble gas signatures and clumped isotope signatures of hydrocarbon and non-hydrocarbon molecules is performed. This interpretation involves determining the type and quality of hydrocarbons and/or depth of a hydrocarbon accumulation and/or volume of a hydrocarbon accumulation. As an example, the noble gases may be utilized to determine hydrocarbon accumulation volume, hydrocarbon type and oil quality and is provided in a U.S. Patent No. 61/616,813. As natural gases and oils are initially devoid of noble gases, the addition of these through interaction with formation water provides information about the samples. The impact of this interaction on isotopic ratios and absolute concentrations of noble gases present in the hydrocarbon phase is a function of three variables: (i) the initial concentration and isotopic signature of noble gases in the water phase, (ii) the solubility of noble gases in water and oil (solubility of noble gases in oil is controlled by oil quality), and (iii) the ratio of the volumes of oil/water, gas/water or gas/oil/water.

The initial concentration of noble gases in the water phase prior to interaction with any hydrocarbons can be accurately measured or estimated. Noble gases dissolve in water during recharge from meteoric waters or at the air/water boundary for seawater. This initial signature is therefore dominated by atmospheric noble gases, namely 20Ne, 36Ar, 84Kr and 132Xe. The amount of noble gases that dissolve into the water phase obeys Henry's Law, which states that the amount of noble gases dissolved in water is proportional to the partial pressure of the noble gases in the atmosphere (which varies as a function of altitude for meteoric water recharge). The Henry's constant is directly related to the salinity of the water phase and the ambient temperature during the transfer of noble gases to the water. Formation waters recharged from meteoric waters at the air/soil interface may have an additional component of atmospheric derived noble gases from that which is expected purely from equilibrium, "excess air". These influences may be subject to adjustments (e.g., correction schemes, such as those noted in Aeschbach-Hertig, W., Peeters, F., Beyerle, U., Kipfer, R. Palaeotemperature reconstruction from noble gases in ground water taking into account equilibrium with entrapped air. Nature, 405, 1040-1044, 2000, for example). The resulting noble gas signature therefore lies between air-saturated water (ASW), air-saturated seawater (ASS) and air-saturated brine (ASB) for any given temperature. Radiogenic noble gases are then introduced following recharge through radioactive decay of minerals within the subsurface. The concentration of the radiogenic noble gases typically increases with increasing formation water residence time (or age). This evolving noble gas signature in the water phase is changed as a result of mixing and interaction with other fluids. The solubilities of noble gases in water have been determined for a range of different temperatures, as is known in the art (e.g., Crovetto, R., Fernandez-Prini, R., Japas, M. L. Solubilities of inert gases and methane in H2O and D2O in the temperature range of 300 to 600K, Journal of Chemical Physics 76(2), 1077-1086, 1982; Smith, S. P. Noble gas solubilities in water at high temperature. EOS Transactions of the American Geophysical Union, 66, 397, 1985.). Similarly, the measured solubility of noble gases in oil increases with decreasing oil density (Kharaka, Y. K. and Specht, D. K. The solubility of noble gases in crude oil at 25-100° C. Applied Geochemistry, 3, 137-144, 1988.). The exchange of atmospheric noble gases between formation water and both the oil and/or gaseous hydrocarbon phase can occur through various processes, and the extent of fractionation induced by each of these processes gives rise to different signatures in the different phases. These processes can be modeled and may comprise equilibrium solubility, Rayleigh style fractionation and gas stripping. The exchange of noble gases between oil and water may result in the oil phase developing an enrichment in the heavy noble gases (Kr and Xe), and an associated depletion in the light noble gases (He and Ne) relative to the water phase. This is because of the greater solubility of the heavier noble gases in oil than in water. In contrast, the interaction of a gas phase with water may result in the gas phase becoming relatively enriched in the lighter noble gases and depleted in the heavy noble gases relative to a water phase. The magnitude of this fractionation may change depending upon the exchange process involved and on the density of the oil phase Assuming that a subsurface signature is preserved during migration to the surface, the phases that interacted (e.g. oil-water, gas-water or gas-oil-water) with a seeped hydrocarbon by measuring the concentration of noble gases in the hydrocarbon sample may be determined. The noble gases provide a conservative tracer of the hydrocarbon type present within the subsurface (oil vs. gas). Knowledge of the solubility of noble gases as a function of oil density provide further information about the estimate of the oil quality when the hydrocarbon present is determined to be oil. Finally, given that two of the three variables that control the exchange of noble gases between water and hydrocarbons are known or can be modeled, the hydrocarbon/water volume ratio within a subsurface hydrocarbon accumulation can be determined. From this it is possible to quantitatively predict the volume of hydrocarbon present within a subsurface accumulation.

In addition to the utilization of noble gases to determine hydrocarbon accumulation volume, hydrocarbon type and oil quality, the clumped isotope geochemistry may be utilized to determine the depth of a hydrocarbon accumulation. As an example, U.S. Patent No. 61/558,822 describes a process for determining the clumped isotope signature of any molecule. The clumped isotope signature of any molecule is a function of (i) temperature-independent randomly populated processes (e.g., stochastic distribution) and (ii) thermal equilibrium isotopic exchange. The latter process is controlled or dependent on the surrounding temperature. The stochastic distribution of any isotopologue can be determined from the bulk isotope signatures of the species from which it derives. For example, determining the stochastic distribution of isotopologues for methane requires knowledge of the 13C and D signatures of methane. The isotopic signature of hydrocarbon gases that are stored in a subsurface accumulation or that are present at seeps may reflect the isotopic signature of the gas generated from the source rock. As such, this signature may be concomitantly determined during the characterization of the hydrocarbons present at a seep and substituted directly in to the calculation of the stochastic distribution. There may be occasions, however, when the isotopic signature of gases is altered by processes like mixing with biogenic gas. In such instances, correction schemes known in the art may be relied upon, such as Chung et al., (1988; H. M. Chung, J. R. Gormly, R. M. Squires. Origin of gaseous hydrocarbons in subsurface environments: theoretical considerations of carbon isotope distribution in M. Schoell (Ed.), Origins of Methane in the Earth. Chem. Geol., 71 (1988), pp. 97-103 (special issue)). The correction scheme may be used to deconvolve such contributions and reach the initial primary isotope signature that should be used in the calculation of the stochastic distribution.

The expected increased abundance, or enrichment, of any given isotopologue or clumped isotope can be modeled or empirically determined for any given temperature. By measuring the clumped isotope and isotopologue signatures of a given molecule, and through knowledge of the stochastic distribution, the enrichment of the measured concentrations relative to the stochastic distribution can be used to determine the temperature in the subsurface from which this molecule is derived.

Hydrocarbons that derive from a subsurface accumulation may retain a clumped isotope signature that more reflects the temperature at which the hydrocarbons were stored in the subsurface. This non-kinetic control on the isotopic exchange reactions in isotopologues of hydrocarbons that originate from a subsurface accumulation arises as a result of the inherently long residence times of hydrocarbons in the subsurface. Through application of a suitable geothermal gradient to the storage temperature derived from the clumped isotope signature, the location (depth) within the subsurface that seep-associated hydrocarbon accumulations reside may be estimated.

As another independent technique useful for the detection of hydrocarbon accumulations and their location or depth, the microbial ecology and biomarker signature of hydrocarbon seeps may be used to determine the depth of a hydrocarbon accumulation and/or the hydrocarbon accumulation volume and/or the hydrocarbon type and oil quality, as described in U.S. Patent No. 61/595,394. Ecology is the study of interactions between living organisms and the non-living surrounding environment. Microbial ecology refers to the ecology of small organisms like bacteria and archaea. Ecology includes biotic parameters like community composition (e.g., which organisms are present), community function (e.g., what those organisms are doing), organism behavior, organism quantity and metabolite production. Additionally, ecology includes abiotic parameters like pH, temperature, pressure and aqueous concentrations of different chemical species. We may measure all or some of these parameters to describe the ecology of a hydrocarbon seep.

Seeps that are connected to hydrocarbon accumulations may have different ecologies than seeps that are not connected to hydrocarbon accumulations.

Microbial ecology involves using genomics and culture based techniques to describe the community composition. (Meta) Genomics, (meta) transcriptomics, (meta) proteomics and lipid measurements can be combined with chemical measurements to determine the community function. Changes in temperature drive changes in community structure and function. Changes in hydrocarbon type and volume present in the accumulation change community structure and function. If a seep is connected to a hydrocarbon accumulation, these ecological differences may be reflected in samples acquired from the seep.

The sediment and fluid samples from in and around a hydrocarbon seep may be collected and appropriately preserved. Changes in the ecology of these samples may reflect the conditions of the subsurface accumulations feeding the seeps. Samples from a seep not connected to a hydrocarbon accumulation may not contain ecological parameters associated with a deep hot hydrocarbon environment.

Then, at block 318, the hydrocarbon accumulation type and quality, depth and volume obtained from the microbial ecology, clumped isotope and noble gas signatures may be integrated with remote sensing data obtained from remote sensing, as noted in blocks 302 to 310, to confirm accumulation materiality. This integration step includes incorporation all aspects of the hydrocarbon system model along with geological and geophysical data, such as basin modeling, and/or probabilistic or statistical risk assessments. Included in this assessment are the risks of adequate source, maturation, migration, reservoir presence and quality, trap size and adequacy, and seal. If aspects of the risk assessment, including the results of blocks 312 to 318, are sufficiently favorable, a decision as to whether to stop or continue the process remains.

The discovery stage includes blocks 320 to 322. At block 320, a determination to access the hydrocarbons based on the measured data and the integrated data is made. This determination may include a variety of economic factors that include the associated costs of drilling a well versus the economic benefits of discovering an accumulation of the size expected at the depth expected incorporating appropriate risks. If the cost benefit is deemed sufficient, then, at block 322, a well is drilled and hydrocarbons are discovered based on the determination. This discovery of hydrocarbons may be similar to block 218 of FIG. 2.

As noted above, these remote sensing and direct measurements may be performed by an underwater vehicle and/or a marine vessel. The measurements may include detecting seep locations via a high-resolution multi-beam survey, as described in Valentine et al. (2010; Valentine D L, Reddy C M, Farwell C, Hill T M, Pizarro O, Yoerger D R, Camilli R, Nelson R K, Peacock E E, Bagby S C, Clarke B A, Roman C N, Soloway M. Asphalt Volcanoes as a Potential Source of Methane to Late Pleistocene Coastal Waters. Nature Geoscience Letters. DOI: 10.1038/NGEO848)) in the Santa Barbara basin. While certain measurements may be performed via a surface vessel, the costs of doing regional surveys with towed tools, especially at depths greater than a few hundred meters, are very high due to the limited speeds that can be achieved while keeping the device near the seabed with manageable tension loads on the support cable. The typical spatial resolution achieved with these towed systems is also low (e.g., on the order of hundreds of meters), compared to the approximate ten meter spatial resolution obtained by using a mass spectrometer and fluorometer incorporated into an underwater vehicle (e.g., AUV). There is also the added complexity and potential source of error that may occur if water samples are collected for shipboard analysis and have not maintained their in situ properties.

To enhance the measurement data, an underwater vehicle may be used to obtain certain data. The underwater vehicle may include an AUV, ROV, towfish or manned submersibles. The different configurations of these AUVs and method of operation may include various different combinations of components to provide the measurement data for a specific survey. The different configurations may be utilized to perform the direct measurements of the target locations, as noted above. These measurements may include analysis of gases or water soluble hydrocarbons dissolved in water as well as phase-separated pockets of hydrocarbons in the water. In addition, the direct measurements may include information about geological features associated with active hydrocarbon seep locations. These underwater vehicles are known in the art, as noted above with regard to pipeline leak detection. See; e.g., R. Camilli, A. Duryea 2007., in Proc. IEEE/MTS OCEANS (IEEE/MTS, Vancouver, Canada, 2007), pp. 1-7 (10.1109/OCEANS.2007.4449412).

As an example, underwater vehicles may include various different chemical sensors. Specifically mass spectrometry and fluorometry may be utilized to conduct surveys to locate hydrocarbons in the marine environment. To enhance the hydrocarbon survey techniques, an AUV may be utilized in a system that can be programmed to conduct autonomous missions to any depth of exploration interest. That is, the system may obtain measurement data near the seafloor that results in unsurpassed seafloor, sub-bottom, and in situ water chemistry resolution in near real time. This real time acquisition may provide additional clarification as to the location of the hydrocarbons.

In another example, the underwater vehicle may include a methane sensor to detect the presence of hydrocarbons near the seabed. This underwater vehicle may also include gravity and magnetic sensors to perform additional data that may be correlated to the methane sensor data. To provide additional enhancements, the measured data may be organized with the location of the underwater vehicle to correlate the measured data with other surveys of the subsurface geology. The chemical sensors can be used to locate anomalous chemistries associated with seeps and seep vents, to map these anomalies relative to geologic features, and to distinguish thermogenic from biogenic gas, and gas from oil. Further, sensors may also be utilized to provide chemical and isotopic analysis of hydrocarbons to determine whether a seep source is thermogenic or biogenic. Each of these different sensors may be included in the underwater vehicle to provide enhancements to the measured data collected and analyzed.

Accordingly, in certain embodiments, underwater vehicles (e.g., unmanned underwater vehicle) may include sensors capable of detecting chemical or physical anomalies that are indicative of hydrocarbon seeps and correlating them to a specific location. The m chemical specificity of applied sensors, particularly underwater mass spectrometry supplemented by a fluorometer, may also provide the discrimination of thermogenic seeps from biogenic seeps and to determine whether the seep is associated with gas, oil, or gas and oil. The sensors may include a mass spectrometer, a methane detector, fluorometer, multibeam echo sounder (MBES), sub-bottom profiler (SBP), side-scan sonar (SSS), and camera [this has been done to some extent in oceanographic research]. Regardless, the sensors may be utilized to map the hydrocarbon types and concentrations, which may be utilized to indicate the presence and surface-subsurface linkages to a hydrocarbon system. In addition, the sensors may differentiate biogenic hydrocarbons from thermogenic hydrocarbons, oil from gas, and provide additional information regarding locations for drop cores or piston cores, and further sampling.

The underwater vehicle provides an enhancement to the ability to locate hydrocarbon seeps efficiently and in a cost-effective manner for a large region. This is accomplished through a combination of direct measurements with the remote sensing instruments. In this manner, the subsurface models can be enhanced and reduce exploration risk. Further, this acquisition of this direct measurement data may be performed inexpensively and efficiently at regional scales. As a result, the exploration process may be enhanced to improve the ability to find and prioritize play extensions.

Figure 4:
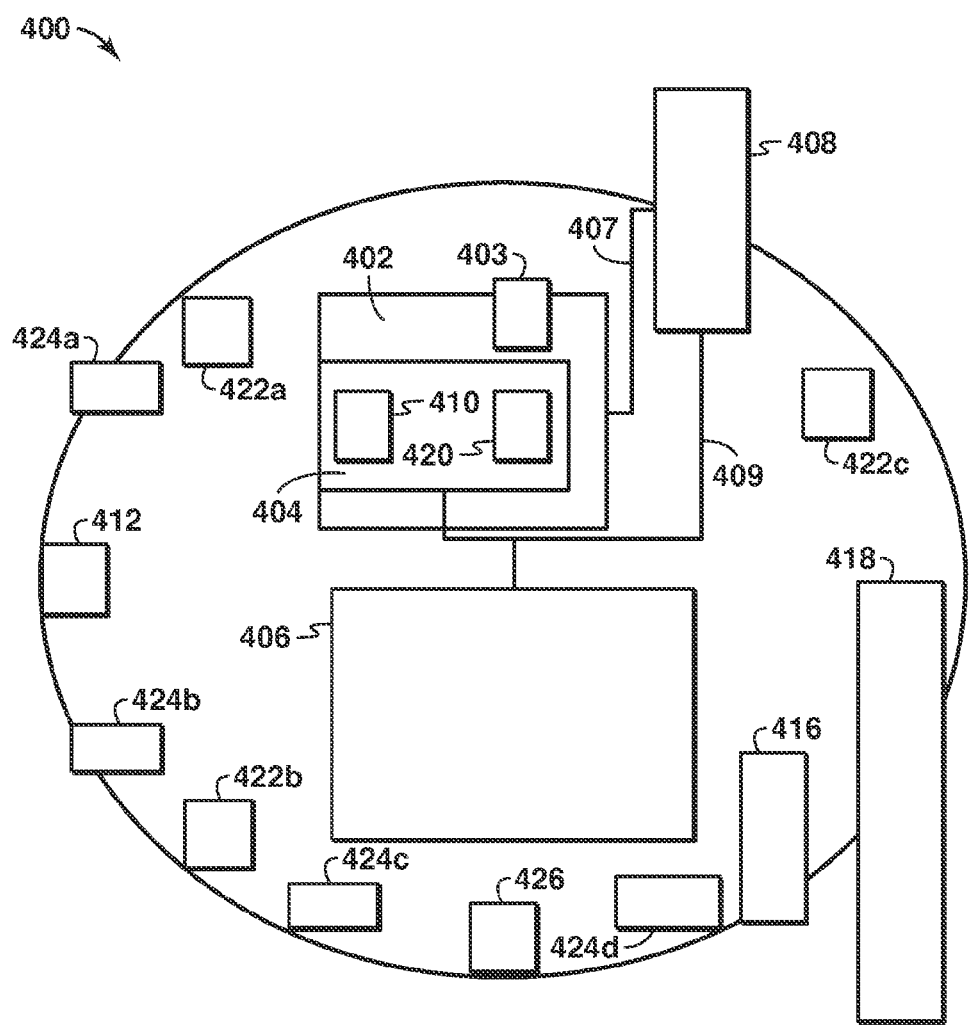
FIG. 4 is a diagram of an AUV in accordance with an exemplary embodiment of the present techniques.

As an example of an AUV, FIG. 4 is a diagram of an AUV in accordance with an exemplary embodiment of the present techniques. In this AUV 400, a process control unit 402 is utilized to manage the navigation components and the measurement components. The process control unit 402 includes a processor 403, memory 404 and sets of instructions (e.g., master navigation module 410 and master measurement module 420) that are stored in the memory 404 and executable by the process control unit 402. The power for the process control unit 402 may be supplied by one or more batteries 406. Also, the process control unit 402 may include a communication component 408, which may include an antenna and other equipment to manage communications with other systems, such as marine vessel and/or GPS.

The navigation components of the AUV 400 may include the master navigation module 410, a mapping component, such as SONAR component 412, motion sensor component 416 and propulsion component 418. The master navigation module may operate by the processor executing the sets of instructions configured to: manage the different navigation components, calculate the path of the AUV, obtain signals (e.g., GPS signals and/or wireless guidance signals), communicate with the propulsion systems to adjust steering and/or speed of the AUV, obtain motion sensor data, and/or calculate the AUV's location based on different data (e.g., GPS data, wireless guidance data, motion sensor data and mapping component data). The SONAR component 412 may include SONAR sensor equipment to send and receive SONAR signals and provide associated SONAR data to the master navigation module. The SONAR component 412 may also be utilized for the detection of hydrocarbons external to the AUV (e.g., in fluid disposed external to the AUV, such as a body of water that the AUV is disposed within). The motion sensor component 416 may include various sensors and other equipment to obtain motion sensor data about the forces applied to the AUV 400 (e.g., currents and fluid flows). The motion sensor component 416 may include a processor that communicates with a gyroscope, depth sensor, velocity meter along with various other meters to measure the orientation or other parameters of the AUV. Also, the propulsion component 418 may include two propeller assemblies enclosed by a propeller support member, a motor coupled to the batteries 406.

The measurement components of the AUV 400 may include the master measurement module 420, resistivity components 422a-422c, camera component 424a-424c and/or other hydrocarbon detection component 426 along with the SONAR component 412. The master measurement module may operate by the processor executing the sets of instructions configured to: manage the different measurement components, determine whether hydrocarbons are present external to the AUV (e.g., in fluid disposed external to the AUV, such as a body of water that the AUV is disposed within), communicate with the propulsion systems to adjust steering and/or speed of the AUV if hydrocarbons are detected, obtain measurement data and the AUV's location based on different hydrocarbon indications, and store certain measurement data and AUV location data. The resistivity components 422a-422c may include various sensor that are configured to detect resistivity via contact with the fluid adjacent to the AUV and provide these measurements to a processor, which is configured to send and receive commands, process the resistivity data and to communicate resistivity data and/or certain notifications with the master measurement module 420. The camera components 424a-424c may include various cameras that are configured to obtain images (e.g., the images may be subjected to different filters) of fluids, bathymetric features, biologic communities, bubbles, etc. adjacent to the AUV path and provide these images to a processor, which is configured to send and receive commands, process the images, and to communicate camera data and/or certain notifications with the master measurement module 420. The other hydrocarbon detection components 426 may include various piping and equipment that is utilized to obtain measurement data near the AUV. The other hydrocarbon detection components may include fluorescence polarization component, fluorometric component, wireless component (e.g., acoustic component and/or SONAR component 412), methane component, temperature component, mass spectrometer component and/or other suitable measurement components. For example, a temperature component typically has a thermocouple or a resistance temperature device (RTD). The measurement data may include acoustic images, acoustic data, temperature data, fluorometric data, and/or polarization data, for example. The other hydrocarbon detection components 426 may also include a processor configured to send and receive commands, to process the measured data, and to communicate measured data and/or certain notifications with the master measurement module 420.

The equipment within the AUV 400 may be coupled together through physical cables to manage the distribution of power from the batteries 406 and to manage communication exchanges between the equipment. As an example, power distribution is provided between the process control unit 402, the one or more batteries 406 and the communication component 408 via lines 409, while the communication distribution is provided between the process control unit 402 and the communication component 408 via line 407. Other communication and power distribution lines are not shown for simplicity in this diagram. Also, the communication between certain devices may be via wireless communications, as well. Accordingly, the specific configuration with the AUV provides flexibility in obtaining different types of data, which may be managed for certain locations.

Multiple different sensors may be preferred to further verify the measured data from one of the sensors. For example, the presence of methane alone does not provide the clear indication of a biogenic gas from thermogenic gas and whether wet gas and/or oil are present. Biogenic gas is not generally a conventional exploration target, although it can be exploited in some environments. The formation of biogenic gas is related to methanogenic bacteria that in some cases reduce $CO_2$ and oxidize organic matter to produce only methane in shallow environments. As such, it is most common to find small amounts of methane ($C_1$) in shallow marine sediments that are insignificant for exploration purposes, effectively acting as a "contaminant" in the absence of other hydrocarbon indicators. Conversely, thermogenic gas is generated from an organic rich source rock at depth that produces a host of hydrocarbon gases ($C_1$-$C_5$) and heavier liquids (oil). The mass spectrometer is capable of analyzing for methane, ethane, propane, and higher hydrocarbons (up to 200 atomic mass units) that provides a distinction between biogenic and thermogenic gas, gas wetness, and whether a seep is related primarily to oil, gas, or both a combination of oil and gas. The fluorometer supplements the mass spectrometer by indicating the presence of aromatic compounds consistent with liquid-rich hydrocarbons.

While the mass spectrometer has the capability of analyzing masses to 200 amu, the sensitivity to lower atomic masses (e.g., <70 amu) is greater. As a result, certain lighter masses (actually mass/charge ratio or m/z) that are generally distinctive for a compound of interest for hydrocarbon exploration may be useful in hydrocarbon exploration. These masses or their ratios relative to a mass that remains generally constant in water are utilized. For example, water with mass 17 represented by 16O1H+ is commonly chosen for this purpose. There is also the added complexity of certain masses not being uniquely distinctive for a single compound. An example is mass 16, which is both a primary mass indicator for methane ($12C_1H_4$) and oxygen (16O). To avoid significant contributions from interfering compounds, methane is measured at mass 15 rather than 16, and commonly compared to mass 17, or amu ratio 15/17 is used to indicate methane amount for a particular measurement. This ratio assumes that any fluctuation in the water ion peak is due to variability in instrument response (e.g., instrument drift) because the concentration of water in water is well known. Some commonly used masses (or ratios relative to mass 17) of importance are listed below in Table 1.

TABLE 1

Commonly used masses (mass/charge ratio) for locating and characterizing hydrocarbon seeps

| m/z | Interpreted Compound | Abbreviation |
|---|---|---|
| 4 | Helium ($He^+$) | He |
| 14 | Nitrogen ($N^+$ and $N_2^{++}$) plus some methane and ethane | NIT |
| 15 | Methane (or methyl $C_1$ fragment) ($CH_3^+$) | MTH or C1 |
| 17 | Water ($^{16}O^1H^+$) | H2O |
| 20 | Water ($H_2^{18}O^+$) | |
| 22 | Carbon dioxide ($CO_2^{++}$) | |
| 28 | Nitrogen ($N_2^+$) | |
| 30 | Ethane (or ethyl $C_2$ fragment) ($C_2H_6^+$); ethane sometimes @27 | ETH or C2 |
| 32 | Oxygen ($^{16}O_2^+$) | O2 |
| 34 | Hydrogen sulfide ($H_2S^+$) and oxygen $^{16}O^{18}O$ | H2S |
| 39 | Propane ($C_3H_8$) various fragments | PRO |
| 40 | Argon ($Ar^+$) | Ar |
| 41 | Propane (or propyl $C_3$ fragment) ($C_3H_7^+$); propane sometimes measured @39 or 43 if no major interferences (e.g., from $CO_2^+$ @ 44) | $C_3^+$ |
| 44 | Carbon dioxide ($CO_2^+$) | CO2 |
| 55 | Naphthene $C_4$ fragment ($C_4H_7^+$) | NAP |
| 57 | Paraffin $C_4$ fragment ($C_4H_9^+$) | PAR |
| 58 | Various "butane" fragments ($C_4H_{10}$) | BUT |
| 60 | Acetic acid ($CH_3COOH^+$), or from carbonyl sulfide ($COS^+$) | HAC |
| 78 | Benzene ($C_6H_6^+$) | BEN |
| 91 | Toluene ($C_7H_7^+$) | TOL |
| 97 | Alkylated Naphthene ($C_7H_{13}^+$) | ANP |
| 106 | Xylene ($C_8H_{10}^+$) | XYL |

The mass spectrometer housed within an AUV may provide the rapid measurement of masses in the range of 1 amu to 200 amu for a water sample about every five seconds, depending on water depth. The presence of $C_1$, $C_2$, $C_3^+$, paraffins, naphthenes, and the aromatics benzene and toluene (sometimes xylene), as well as the non-hydrocarbon gases $CO_2$, $H_2S$, $N_2$, Ar, and He, or their ratios, provides beneficial interpretations to be made regarding the location and characterization of hydrocarbon seeps. A biogenic gas consists only of methane (occasionally very small amounts of ethane) and is called a "dry" gas. Thermogenic gas usually has varying amounts of heavier or higher hydrocarbons of C2-C5 and is called a "wet" gas.

TABLE 2

Ratios used to determine whether a source contains dry or wet gas with MS.

| | Dry Gas | Wet Gas |
|---|---|---|
| ($C_2/C_1$)1000 | <8 | >8 |
| $C_1/(C_2 + C_3)$ | >100 | <100 |

Table 2 shows general guidelines for distinguishing dry gas from wet gas with mass spectrometric measurements. Dry gas can also be thermogenic, derived from very mature source rocks. The mass spectrometric data may allow the distinction between a dry biogenic gas, which is characterized by a greater relative amount of 12C, and a dry thermogenic gas characterized by a relatively greater amount of 13C. Wet gases may be associated with oils. Greater amounts of the higher mass compounds, such as amu 55 (naphthenes) and 57 (paraffins) and the water soluble aromatics benzene, toluene, and xylene are more indicative of oil seeps. Also, the 57/55 ratio can be used to determine whether leaking hydrocarbon accumulations contain oil, wet gas, or dry gas. Paraffin/naphthene (57/55) ratios of <0.5 are indicative of biodegraded heavy oils, ratios of 0.5-2.0 are characteristic for normal oils, ratios of 2 to 4 are typical of wet gas or condensate, and ratios >4 indicate dry gas. The fluorometer supplements the mass spectrometer by detecting aromatic compounds; that locate predominantly oil seeps. Conversely, the mass spectrometer complements the fluorometer in that recent organic matter (e.g., unassociated with thermogenic hydrocarbons) strongly fluoresces and is a common contaminant detected by the fluorometer. However, no significant hydrocarbon responses may be detected by mass spectrometry associated with recent organic matter. Large mass spectrometer responses for the non-hydrocarbon gases $CO_2$, $H_2S$, or $N_2$, with or without hydrocarbons, may indicate leaking fluids associated with trapped accumulations dominated by these generally non-economic gases that compete for trap space with migrating hydrocarbons. These chemical measurements provide the risks for associated non-hydrocarbon gases to be assessed in an exploration program.

Accordingly, in one or more embodiments, an unmanned underwater vehicle may be equipped with sensors to detect and locate hydrocarbons seeping from the seafloor into the water column. The location of thermogenic hydrocarbon seeps indicate an active hydrocarbon system. Chemical sensors, which may specifically include a mass spectrometer and fluorometer, may be utilized to distinguish between thermogenic and biogenic hydrocarbon sources.

As a specific example, the unmanned vehicle may be an AUV. The AUV may survey a regional area (e.g., an areas of interest) by collecting sub-bottom profiles, bathymetry, and backscatter along line of travel, and using the data to resolve features less than 1 m across. Simultaneously, the AUV may analyze water chemistry with onboard mass spectrometer roughly every 5 seconds for spatial resolution of about 10 m. The AUV may also measure acoustic sensitivity relative to surface vessel acoustics, which may be beneficial in deep water surveys. Then, the chemistry, near-surface geology, and seismic interpretations may be combined, mapped, and integrated into a subsurface model. With this subsurface model, the measured data may be utilized to track areas of potential geologic interest (e.g., faults, stratigraphic pinchouts, fluid escape features), locate active gas/oil seepage vent locations, which may be further sampled for additional direct measurement data. This process may provide information to correlate seeps to subsurface migration pathways.

In one or more embodiments, different sensors may be utilized to detect bubbles near and within the body of water. For example, bathymetric or acoustic backscatter expressions may be utilized to detect potential seeps through the detection of bubbles escaping from the seafloor. Similarly, bubbles related to hydrocarbons from active seeps may be detected via the seismic or acoustic properties of the bubbles relative to the surrounding seawater.

In certain embodiments, the acoustic backscatter data may also reveal anomalous seafloor reflectivity that can locate carbonate hardgrounds, microbial mats, or black iron sulfides that are consistent with biological processes where hydrocarbons are consumed or produced at seeps.

In other embodiments, bathymetric expressions may include pockmarks, mud volcanoes, faults, etc. These measured data may indicate potential hydrocarbon migration pathways from the subsurface to the seafloor.

In one or more embodiments, the mass spectrometer may be utilized to provide in situ chemical detection using the membrane-inlet mass spectrometer (MIMS). In this system, fluid is passed across a membrane on one side, while a vacuum is drawn on the other side. Hydrocarbons and other gases pass across the membrane into the instrument due to the pressure gradient, where they are ionized and separated by their mass-to-charge ratio. The MIMS systems may be sensitive to chemical species up to 200 amu in mass; sensitivity is generally better for lighter compounds. See, e.g., (Camilli R C, Duryea A N. 2009. Characterizing Spatial and Temporal Variability of Dissolved Gases in Aquatic Environments with in situ Mass Spectrometry. Environmental Science and Technology 43(13):5014-5021.) and SRI (Bell, R. J., R. T. Short, F. H. W. van Amerom, and R. H. Byrne. 2007. Calibration of an in situ membrane inlet mass spectrometer for measurements of dissolved gases and volatile organics in seawater. Environ. Sci. Technol. 41:8123-8128 [doi:10.1021/es070905d]). The methane and higher order hydrocarbons are detectable down to the ppb level, which may be collected continuously over five second intervals. This interval defines the spatial resolution of the sensor, which is determined in conjunction with the speed of the underwater vehicle. Simultaneous detection of multiple species of hydrocarbons is useful in determining whether the source is thermogenic or biogenic. The limit of detection for these systems is listed between 20 nM and 56 nM for methane. These instruments analyze species dissolved in the water and not the composition of bubbles. It is expected that the concentration of dissolved hydrocarbons may be greater near seeps or bubble plumes containing hydrocarbons. It is also expected that thermogenic hydrocarbons may be distinguishable from biogenic hydrocarbons based on the mass spectrum. A C1:(C2+C3) ratio, combined with the proportion of 13C, was linked to the nature of the source as described in the reference Sackett W M. 1977. Use of Hydrocarbon Sniffing in Offshore Exploration. Journal of Geochemical Exploration 7:243-254. The MIMS system may enhance the success rate of any drop core surveys, seismic or other testing in locations where thermogenic hydrocarbons are detected.

In one or more embodiments, one or more methane sensors may be utilized. Methane sensors are based on conductivity or infrared spectroscopy. Certain methane sensors pass fluid across a supported silicone membrane into a chamber that contains oxygen and a tin oxide element. When the methane adsorbs onto a layer of tin oxide, it interacts with oxygen present in the sensing cavity. This interaction changes the resistance measured across the device. The sensor responds slowly and may not reach equilibrium if being towed. However, the concentration above a seep may cause the signal to spike in less than one minute (Lamontagne R A, Rose-Pehrsson S L, Grabowski K E, Knies D L. 2001. Response of METS Sensor to Methane Concentrations Found on the Texas-Louisiana Shelf in the Gulf of Mexico. Naval Research Laboratory report NRL/MR/6110-01-8584.). As the gas diffuses via Henry's law, the difference in the partial pressure of methane across the membrane drives the influx of methane across the sensor in both directions. The reliance on diffusion slows the equilibrium time of the sensor, which results in less spatial resolution as compared to a mass spectrometer. It may be that only spikes observed in the data are used as confirmations of seep locations. As another example, the methane sensor may be based on infrared (IR) spectroscopy. In this system, a laser is tuned to the near-IR absorption band specific for methane. The sensor response time is similar to the methane sensor described above. Other methane sensors may utilize a vacuum to pass methane through a membrane. The separation across the membrane reduces interference from fluid during the analysis and may provide more resolution, but fails to distinguish between thermogenic and biogenic sources.

In one or more embodiments, one or more fluorometry sensors may be utilized. These sensors utilize aromatic hydrocarbons that emit fluorescence when excited in the UV (generally due to a $\pi$-$\pi$* electronic absorption) with certain regions being significantly "brighter" than regions that do not contain aromatics. As certain saturated hydrocarbons do not emit fluorescent photons when excited with UV light (e.g., methane, ethane, propane), this sensor is useful for seeps containing benzene, toluene, and xylene, for example. Though fluorometry provides no specific identification of hydrocarbons present, it may be utilized with other sensors to indicate a thermogenic source. As fluorescence is an efficient chemical process, limits of detection can be on the order of several pM (i.e. 0.004 nM).

Further, the sensors may be utilized to differentiate hydrocarbon seeps based on a differencing with background values and/or differentiate the seepage levels. That is, the present techniques may reliably distinguish background from anomalous hydrocarbon chemistries in water and may also provide a level of seepage from the source. For example, once potential seeps have been identified in a target location, the autonomous underwater vehicle carrying appropriate sensors (e.g., mass spectrometer, fluorometer, etc.) may distinguish anomalous hydrocarbon amounts from background values and thus reliably detect hydrocarbon seepage. Also, in areas with no seepage, the present techniques may reduce or eliminate false positives by detection of specific chemical markers. For example detection of ethene and propene may be indicative of contamination of water from refined and combusted hydrocarbons, or detection of aromatics from recent organic matter. In areas of low seepage, the subtle seep characteristics may be reliably detected. These subtle chemical anomalies may rely upon the acquisition parameters, and background chemical conditions to differentiate the hydrocarbons for detection. In this manner, potential seeps that do not yield chemical anomalies can be eliminated from a list of potential seep locations. This may reduce additional follow-up operations for these areas (e.g., drop or piston cores, gas and fluid samples), which further enhances the efficiency of the process.

With these detected anomalies, a map or model may be formed on a grid basis or mapped autonomously through artificial intelligence encoded within the underwater vehicle. Mapped anomalies can be used to locate the seep discharge zone and to relate hydrocarbon leakage to areal geologic features, such as along fault zones or at stratigraphic pinchouts adjacent to a basin margin. The mapping may also include the geochemical characteristics of the anomaly to distinguish biogenic from thermogenic seeps, gas from oil, gas wetness, and oil quality (e.g., the approximate API gravity).

In one or more embodiments, potential hydrocarbon seeps can be screened (either from ship mounted detectors or from detectors within the AUV) using a combination of multi-beam echo sounder (MBES) to detect sea bottom topography, texture, and density, while a sub-bottom profiler can locate shallow subsurface gas anomalies and hydrate layers associated with bottom simulating reflectors. We suggest that chemical sensors can be used to locate anomalous chemistries associated with seeps and seep vents, to map these anomalies relative to geologic features, and to distinguish thermogenic from biogenic gas, and gas from oil.

A two-tiered approach may be utilized where, for example, a 100,000 km$^2$ area is screened for hydrocarbon seepage using improved geophysical techniques followed by fully-autonomous AUVs equipped with low power chemical and acoustic sensors. These autonomous AUVs could also be shore-launched or vessel-launched as propulsion and sensor technologies improve. It might even be possible to deploy the AUVs from the air. Higher resolution acoustic tools (MBES) for bathymetry imaging, seafloor surface texture, and bubble detection in the water column are possibly required for screening of seeps in deeper water environments. Once seep screening is achieved, a coordinated group of low power AUVs equipped with a mass spectrometer, fluorometer and acoustic (SBP, SSS) sensors would follow up with missions to detect and map HC anomalies, coordinated with all previous geologic data. This approach could be used to answer basic questions about active HC systems, acreage selectivity, and play extensions. More specific applications also include locations of seafloor vents for follow-up sampling for clumped isotope, noble gas, and microbial ecology linkages of seepage zones along the locations of geologic features (e.g., faults, stratigraphic pinchouts) to subsurface migration pathways, or for use in special environments such as under ice in areas with limited seasonal opportunities for surface vessel surveys. This method requires low power AUVs capable of coordinated missions operating autonomously with precise positioning capability, immense data logging/transmission capability, and with the additional challenge of using high power acoustic sensors. Given the large areal extent, physical sensors that can survey several thousand square kilometers relatively quickly appear to have a better chance of success than purely chemical sensors (a technique such as ocean acoustic waveguide remote sensing (OAWRS), for example).

In addition for certain configurations, multiple measurement components (e.g., different hydrocarbon detection sensors) can further enhance the measurement confidence of the hydrocarbon detection. For example, some of the components (e.g., sensors) may not detect hydrocarbons in certain environments. As a specific example, a camera may not detect hydrocarbons if the hydrocarbon droplets are too small and dispersed, as it may indicate other floating debris. However, the camera may easily identify microbial mats associated with hydrocarbons that commonly exhibit large color contrasts with the surrounding seafloor. Similarly, wireless sensors (e.g., acoustic or SONAR sensors) may record signals (e.g., electromagnetic, acoustic or other) that are not generated by seeps, but result from subsea equipment or animals. However, if an acoustic sensor detects certain signals or sounds that indicate a hydrocarbon seep, then a mass spectrometer, methane detector or camera, etc. may be utilized to confirm the leak (e.g., presence of hydrocarbons). Thus, the use of multiple sensors may reduce the likelihood of erroneous seep detection.

As a further enhancement, the AUVs may be utilized to expedite the survey of a region with potential seep locations. As an example, two or more AUVs may be deployed by a single vessel within an area to cover discrete sections or segments of the area based upon geologic features that may provide migration pathways (e.g., fault traces on the seafloor, interfaces between salt features and surrounding sediments). By distributing the AUVs along these potential seep locations, which may overlap, the AUVs may be utilized to survey the region in less time than previous survey techniques. That is, the region may be divided into various sections, based on more favorable areas for seep locations from geologic reasoning, for each of the AUVs. As a result, different sections may be monitored concurrently.

Figure 5:
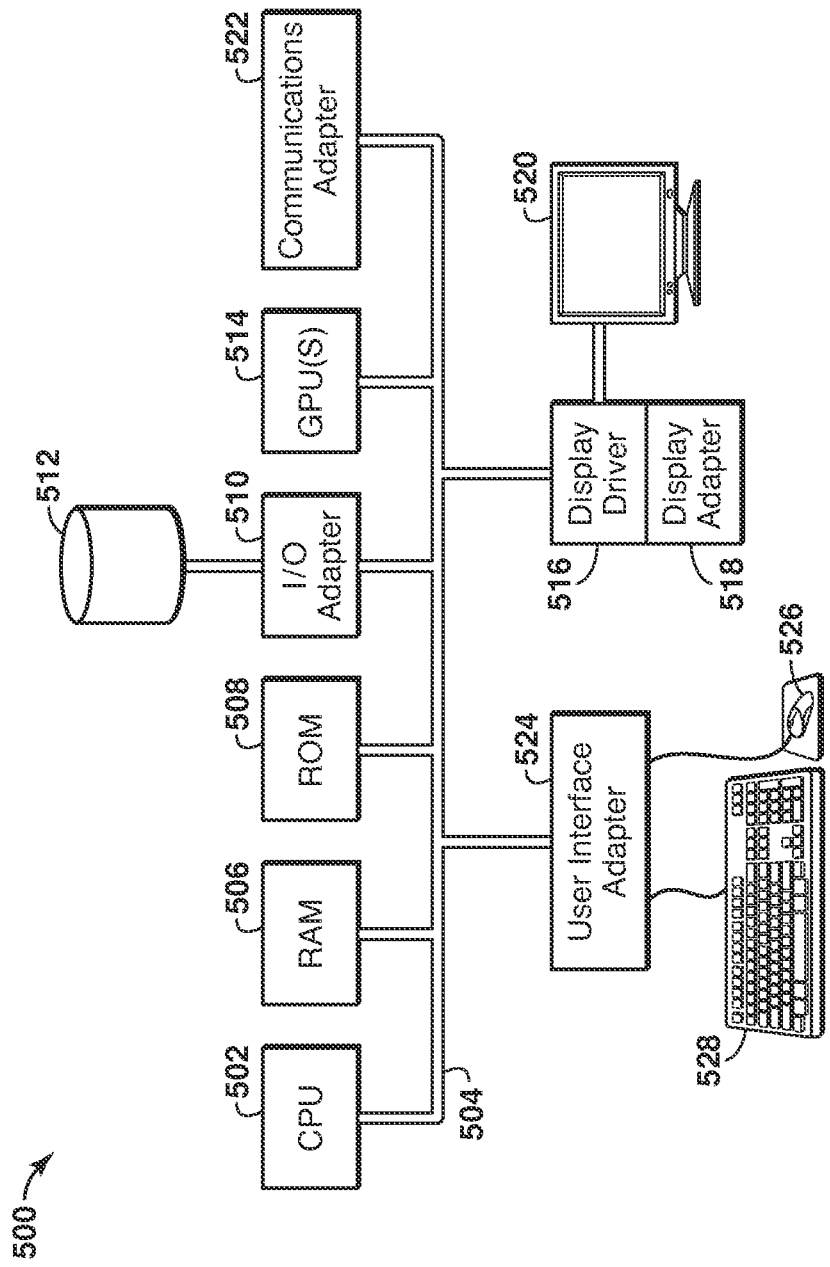
FIG. 5 is a block diagram of a computer system that may be used to perform any of the methods disclosed herein.

As an example, FIG. 5 is a block diagram of a computer system 500 that may be used to perform any of the methods disclosed herein. A central processing unit (CPU) 502 is coupled to system bus 504. The CPU 502 may be any general-purpose CPU, although other types of architectures of CPU 502 (or other components of exemplary system 500) may be used as long as CPU 502 (and other components of system 500) supports the inventive operations as described herein. The CPU 502 may execute the various logical instructions according to disclosed aspects and methodologies. For example, the CPU 502 may execute machine-level instructions for performing processing according to aspects and methodologies disclosed herein.

The computer system 500 may also include computer components such as a random access memory (RAM) 506, which may be SRAM, DRAM, SDRAM, or the like. The computer system 500 may also include read-only memory (ROM) 508, which may be PROM, EPROM, EEPROM, or the like. RAM 506 and ROM 508 hold user and system data and programs, as is known in the art. The computer system 500 may also include an input/output (I/O) adapter 510, a communications adapter 522, a user interface adapter 524, and a display adapter 518. The I/O adapter 510, the user interface adapter 524, and/or communications adapter 522 may, in certain aspects and techniques, enable a user to interact with computer system 500 to input information.

The I/O adapter 510 preferably connects a storage device(s) 512, such as one or more of hard drive, compact disc (CD) drive, floppy disk drive, tape drive, etc. to computer system 500. The storage device(s) may be used when RAM 506 is insufficient for the memory requirements associated with storing data for operations of embodiments of the present techniques. The data storage of the computer system 500 may be used for storing information and/or other data used or generated as disclosed herein. The communications adapter 522 may couple the computer system 500 to a network (not shown), which may enable information to be input to and/or output from system 500 via the network (for example, a wide-area network, a local-area network, a wireless network, any combination of the foregoing). User interface adapter 524 couples user input devices, such as a keyboard 528, a pointing device 526, and the like, to computer system 500. The display adapter 518 is driven by the CPU 502 to control, through a display driver 516, the display on a display device 520. Information and/or representations of one or more 2D canvases and one or more 3D windows may be displayed, according to disclosed aspects and methodologies.

The architecture of system 500 may be varied as desired. For example, any suitable processor-based device may be used, including without limitation personal computers, laptop computers, computer workstations, and multi-processor servers. Moreover, embodiments may be implemented on application specific integrated circuits (ASICs) or very large scale integrated (VLSI) circuits. In fact, persons of ordinary skill in the art may use any number of suitable structures capable of executing logical operations according to the embodiments.

In one or more embodiments, the method may be implemented in machine-readable logic, set of instructions or code that, when executed, performs a method to determine and/or estimate the presence and information, such as depth, type, quality, volume and location of the subsurface hydrocarbon accumulation from a sample related thereto. The code may be used or executed with a computing system such as computing system 500. The computer system may be utilized to store the set of instructions that are utilized to manage the data, the different measurement techniques, the operation of the vehicles and/or the sensor or measurement components, and other aspects of the present techniques.

Other embodiments are described in the following paragraphs:

1. A method for detecting hydrocarbons comprising: performing a remote sensing survey of a survey location; analyzing the remote sensing data from the remote sensing survey to determine a target location; deploying an underwater vehicle (UV) into a body of water; navigating the UV within the body of water to the target location; obtaining measurement data within the body of water at the target location; determining whether hydrocarbons are present at the target location based on the measurement data.

2. The method of paragraph 1, wherein performing the remote sensing survey comprises creating satellite imagery of the survey location.

3. The method of any one of paragraphs 1 to 2, wherein performing the remote sensing survey comprises navigating an airborne vehicle to obtain an airborne survey of the survey location.

4. The method of any one of paragraphs 1 to 3, wherein remote sensing survey comprises performing one or more of ocean acoustic waveguide survey; water column seismic survey; active acoustic sensing survey; imagery and spectroscopy of slicks and atmospheric gas plumes; passive acoustic sensing survey; magnetic and gravity surveys; optical sensing survey and thermal anomalies detection survey.

5. The method of any one of paragraphs 1 to 4, wherein performing the remote sensing survey comprises imaging the survey location via one or more of multibeam echo sounder and sub-bottom profiler via a marine surface vessel or underwater vehicle that also includes side-scan sonar.

6. The method of any one of paragraphs 1 to 5, further comprising determining the concentration of one or more of thermogenic methane, ethane, propane, butane, other alkanes, aromatics, and non-hydrocarbon gases from the measurement data.

7. The method of any one of paragraphs 1 to 6, comprising conducting a drop and piston core sampling technique based on the obtained measurement data within the body of water at the target location.

8. The method of any one of paragraphs 1 to 7, comprising measuring one or more of a pH concentration and an oxidation state in the body of water.

9. The method of any one of paragraphs 1 to 8, comprising measuring magnetic anomalies via multicomponent magnetometers or gravity anomalies via a gravimeter.

10. The method of any one of paragraphs 1 to 9, comprising obtaining biological and chemical sampling of one or more of fluids, gases, and sediments to determine depth, type, quality, volume and location of a subsurface hydrocarbon accumulation from the measurement data.

11. The method of any one of paragraphs 1 to 10, comprising measuring molecular and isotopic signatures of non-hydrocarbon gases and hydrocarbons in the body of water.

12. The method of any one of paragraphs 1 to 11, comprising creating one or more of a chemical map and a physical map of anomalies within the body of water to locate hydrocarbon seep vents.

13. The method of any one of paragraphs 1 to 12, comprising obtaining a sample associated with a subsurface hydrocarbon accumulation; and determining the noble gas signature of the sample, wherein determining the noble gas signature comprises: measuring or modeling an initial concentration of atmospheric noble gases present in formation water in contact with the subsurface hydrocarbon accumulation; modifying the measured/modeled initial concentration by accounting for ingrowth of radiogenic noble gases during residence time of the formation water; measuring concentrations and isotopic ratios of atmospheric noble gases and radiogenic noble gases present in the sample; comparing the measured concentrations and isotopic ratios of the atmospheric noble gases and the radiogenic noble gases present in the sample to the measured/modified modeled concentrations of the formation water for a plurality of exchange processes; determining a source of hydrocarbons present in the sample; comparing an atmospheric noble gas signature measured in the hydrocarbon phase with the measured/modified modeled concentration of the atmospheric noble gases in the formation water for the plurality of exchange processes; and determining at least one of a type of hydrocarbons in the subsurface accumulation, a quality of hydrocarbons in the subsurface accumulation, a hydrocarbon/water volume ratio in the subsurface accumulation prior to escape to the surface, and a volume of the subsurface accumulation.

14. The method of any one of paragraphs 1 to 12, comprising obtaining a sample associated with a subsurface hydrocarbon accumulation; and determining the clumped isotope signature of the sample wherein determining the clumped isotope signature of the sample comprises: determining an expected concentration of isotopologues of a hydrocarbon species; modeling, using high-level ab initio calculations, an expected temperature dependence of isotopologues present in the sample; measuring a clumped isotopic signature of the isotopologues present in the sample; comparing the clumped isotopic signature with the expected concentration of isotopologues; determining, using said comparison, whether hydrocarbons present in the sample originate directly from a source rock or whether the hydrocarbons present in the sample have escaped from a subsurface accumulation; determining the current equilibrium storage temperature of the hydrocarbon species in the subsurface accumulation prior to escape to the surface; and determining a location of the subsurface accumulation.

15. The method of paragraph 14, wherein determining an expected concentration of isotopologues includes determining a stochastic distribution of isotopologues of the hydrocarbon species for a given bulk isotopic signature for the species.

16. The method of any one of paragraphs 1 to 12, obtaining a sample associated with a subsurface hydrocarbon accumulation; and characterizing the ecology signature of the sample, wherein characterizing the ecology signature of the sample comprises: using a first plurality of analyses to determine a community structure of an ecology of the sample; using a second plurality of analyses to determine a community function of the ecology of the sample; using the community structure and the community function to determine whether the ecology of the sample matches a characteristic ecology of a hydrocarbon system; and when the ecology of the sample matches the characteristic ecology, identifying the sample as part of a hydrocarbon system associated with the subsurface hydrocarbon accumulation.

It should be understood that the preceding is merely a detailed description of specific embodiments of the invention and that numerous changes, modifications, and alternatives to the disclosed embodiments can be made in accordance with the disclosure here without departing from the scope of the invention. The preceding description, therefore, is not meant to limit the scope of the invention. Rather, the scope of the invention is to be determined only by the appended claims and their equivalents. It is also contemplated that structures and features embodied in the present examples can be altered, rearranged, substituted, deleted, duplicated, combined, or added to each other. The articles "the", "a" and "an" are not necessarily limited to mean only one, but rather are inclusive and open ended so as to include, optionally, multiple such elements.

The invention claimed is:

1. A method for detecting hydrocarbons comprising:
    performing a remote sensing survey of a survey location;
    analyzing the remote sensing data from the remote sensing survey to determine a target location;
    deploying an underwater vehicle (UV) into a body of water;
    navigating the UV within the body of water to the target location;
    obtaining measurement data within the body of water at the target location, wherein measurement components on the underwater vehicle measure molecular and isotopic signatures of non-hydrocarbon gases and hydrocarbons in the body of water at the target location and wherein measuring the isotopic signature of hydrocarbons includes measuring the signature of clumped isotopologues in a sample from the body of water; and
    determining whether hydrocarbons are present at the target location based on the measurement data.

2. The method of claim 1, wherein performing the remote sensing survey comprises creating satellite imagery of the survey location.

3. The method of claim 1, wherein performing the remote sensing survey comprises navigating an airborne vehicle to obtain an airborne survey of the survey location.

4. The method of claim 1, wherein remote sensing survey comprises performing one or more of ocean acoustic waveguide survey; water column seismic survey; active acoustic sensing survey; imagery and spectroscopy of slicks and atmospheric gas plumes; passive acoustic sensing survey; magnetic and gravity surveys; optical sensing survey and thermal anomalies detection survey.

5. The method of claim 1, wherein performing the remote sensing survey comprises imaging the survey location via one or more of multibeam echosounder and sub-bottom profiler via a marine surface vessel or underwater vehicle that also includes side-scan sonar.

6. The method of claim 1, further comprising determining the concentration of one or more of thermogenic methane, ethane, propane, butane, other alkanes, aromatics, and non-hydrocarbon gases from the measurement data.

7. The method of claim 1, comprising conducting a drop and piston core sampling technique based on the obtained measurement data within the body of water at the target location.

8. The method of claim 1, comprising measuring one or more of a pH concentration and an oxidation state in the body of water.

9. The method of claim 1, comprising measuring magnetic anomalies via multicomponent magnetometers or gravity anomalies via a gravimeter.

10. The method of claim 1, comprising obtaining biological and chemical sampling of one or more of fluids, gases, and sediments to determine depth, type, quality, volume and location of a subsurface hydrocarbon accumulation from the measurement data.

11. The method of claim 1, comprising creating one or more of a chemical map and a physical map of anomalies within the body of water to locate hydrocarbon seep vents.

12. The method of claim 1, wherein measuring the isotopic signatures of non-hydrocarbon gases and hydrocarbons includes measuring the signature of isotopologues in a sample from the body of water.

* * * * *